United States Patent
Tarler

(10) Patent No.: US 10,226,591 B1
(45) Date of Patent: Mar. 12, 2019

(54) METHODS AND DEVICES FOR CARBON DIOXIDE-BASED SLEEP DISORDER THERAPY

(71) Applicant: Cleveland Medical Devices Inc., Cleveland, OH (US)

(72) Inventor: Matthew D. Tarler, Westlake, OH (US)

(73) Assignee: Cleveland Medical Devices Inc., Cleveland, OH (US)

(*) Notice: Subject to any disclaimer, the term of this patent is extended or adjusted under 35 U.S.C. 154(b) by 1730 days.

(21) Appl. No.: 13/626,011

(22) Filed: Sep. 25, 2012

(51) Int. Cl.
*A61M 16/00* (2006.01)
*A61M 16/12* (2006.01)
*A61M 16/10* (2006.01)
*A61M 16/06* (2006.01)
*A61M 16/08* (2006.01)

(52) U.S. Cl.
CPC ........ *A61M 16/0045* (2013.01); *A61M 16/12* (2013.01); *A61M 16/122* (2014.02); *A61M 16/06* (2013.01); *A61M 16/0883* (2014.02); *A61M 16/10* (2013.01); *A61M 2016/103* (2013.01); *A61M 2202/0225* (2013.01)

(58) Field of Classification Search
CPC .. A61M 16/00; A61M 16/0045; A61M 16/06; A61M 16/08; A61M 16/0883; A61M 16/0891; A61M 16/12; A61M 16/122; A61M 16/10; A61M 2016/103; A61M 2202/0225; A61M 2230/43; A61M 2230/432
See application file for complete search history.

(56) References Cited

U.S. PATENT DOCUMENTS

| | | | |
|---|---|---|---|
| 4,054,133 A * | 10/1977 | Myers ................... | A61M 16/20 128/204.26 |
| 4,188,946 A | 2/1980 | Watson et al. | |
| 5,647,345 A | 7/1997 | Saul | |
| 5,937,858 A | 8/1999 | Connell | |
| 6,622,725 B1 * | 9/2003 | Fisher et al. ............. | 128/204.21 |
| 6,752,150 B1 | 6/2004 | Remmers et al. | |
| 7,073,501 B2 | 7/2006 | Remmers et al. | |
| 7,886,740 B2 * | 2/2011 | Thomas et al. .......... | 128/204.23 |
| 7,900,626 B2 | 3/2011 | Daly | |
| 7,942,824 B1 | 5/2011 | Kayyali et al. | |

(Continued)

OTHER PUBLICATIONS

Y. Mebrate et al., "Dynamic CO2 therapy in periodic breathing: a modeling study to determine optimal timing and dosage regimes," Journal of applied physiology, vol. 107, Issue 3, pp. 696-706. 2009. United States.

*Primary Examiner* — Michael Tsai
(74) *Attorney, Agent, or Firm* — Brian Kolkowski

(57) ABSTRACT

The present invention pertains to a system, method, and device for treating sleep disorders. The present invention is particularly useful in the delivery of carbon dioxide ($CO_2$) to a subject and in the treatment of sleep apnea. Furthermore, integration of components with various sensors and apparatuses associated therewith and attached thereto preferably complete a rebreathing circuit in the present invention. In various embodiments of the present invention where the above components are integrated as a rebreathing circuit, a subject is both the source and recipient of a controlled concentration of carbon dioxide. In such embodiments, treatment of sleep disorders becomes much more efficient and effective.

19 Claims, 12 Drawing Sheets

(56) References Cited

U.S. PATENT DOCUMENTS

2008/0302364 A1* 12/2008 Garde et al. ............. 128/204.23
2010/0147302 A1    6/2010 Selvarajan et al.
2013/0109993 A1*  5/2013 O'Connor ................... 600/533

* cited by examiner

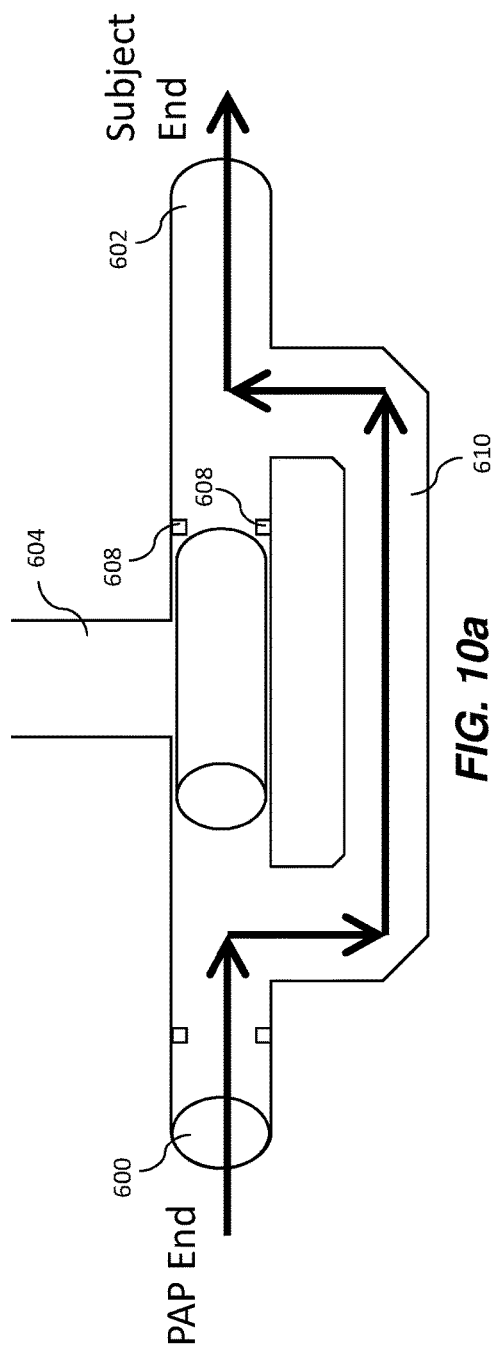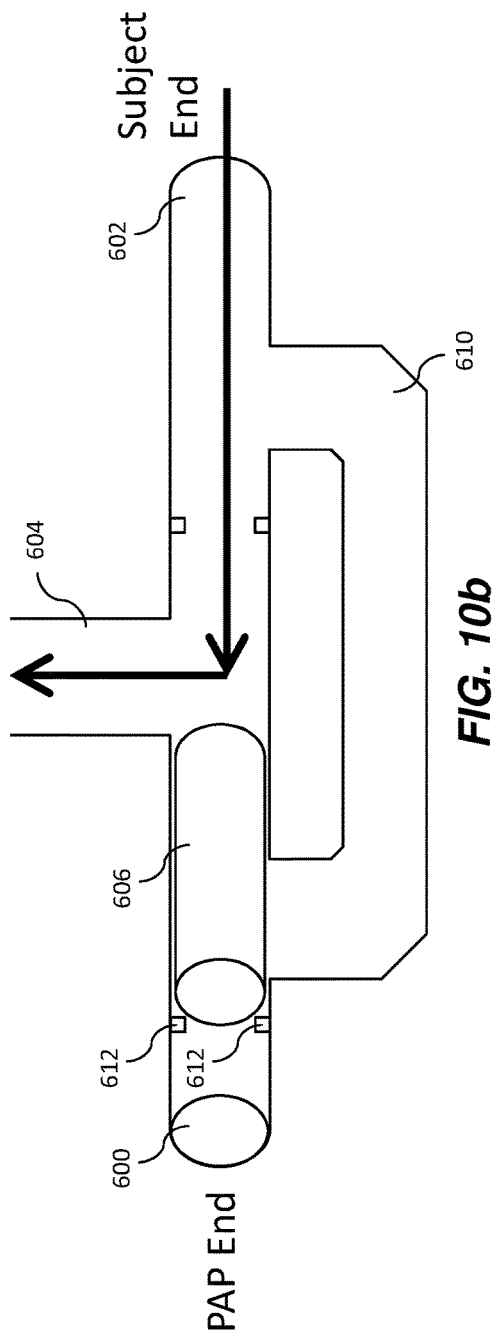

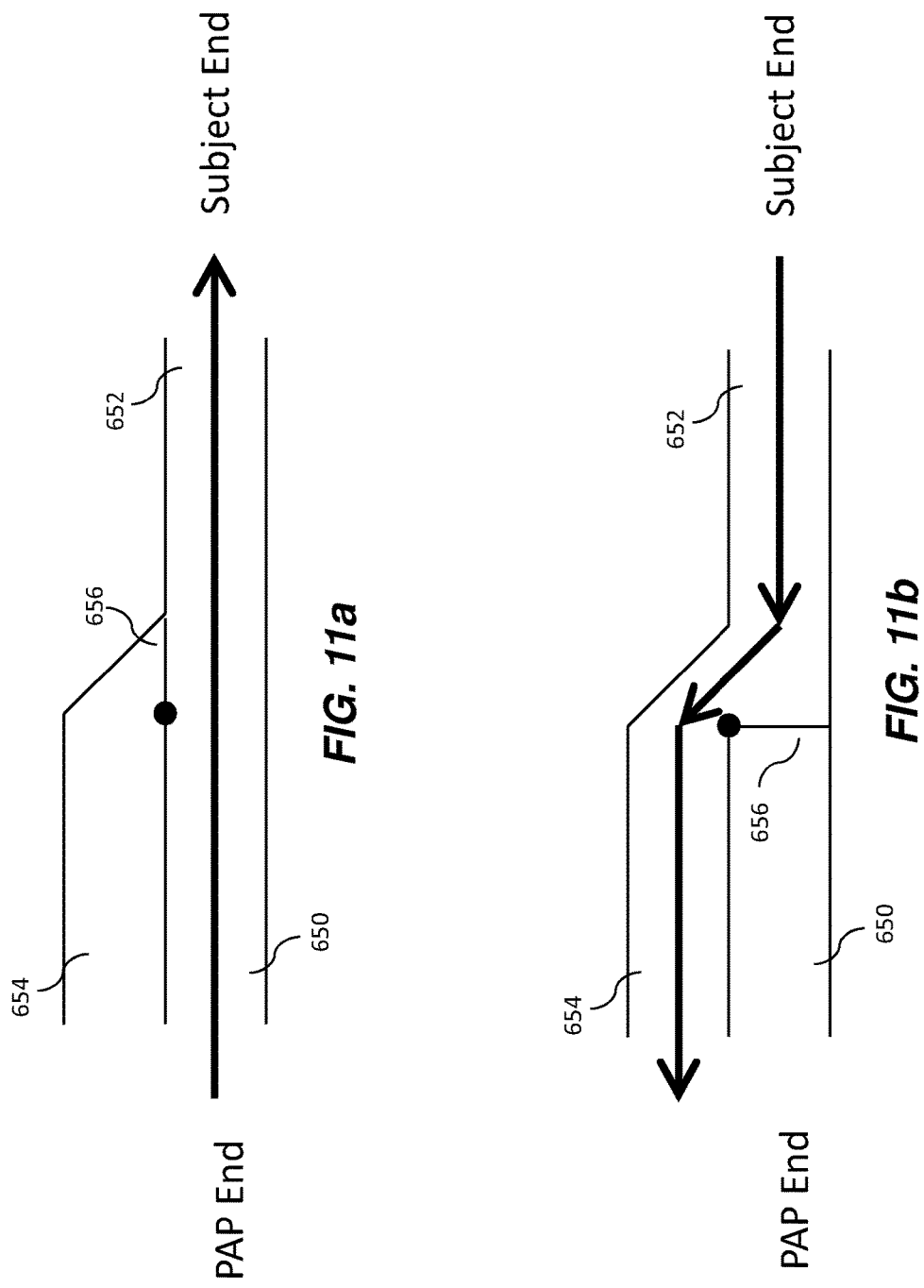

METHODS AND DEVICES FOR CARBON DIOXIDE-BASED SLEEP DISORDER THERAPY

STATEMENT REGARDING FEDERALLY SPONSORED RESEARCH OR DEVELOPMENT

The U.S. Government has a paid-up license in this invention and the right in limited circumstances to require the patent owner to license others on reasonable terms provided for by the terms of grant number 1R43HL097452-01A2 awarded by the National Institutes of Health, National Heart, Lung and Blood Institute.

BACKGROUND OF THE INVENTION

The present invention pertains to a system, method, and device for treating sleep disorders. The present invention is particularly useful in the delivery of carbon dioxide ($CO_2$) to a subject and in the treatment of sleep apnea. In various embodiments of the present invention where components are integrated as a rebreathing circuit, a subject is the source and recipient of a controlled volume of a specific concentration of carbon dioxide. In such embodiments, when at least one component is a positive airway pressure device, ventilator, or the like, treatment of sleep disorders becomes much more efficient and effective.

Nearly one in seven people in the United States suffer from some type of chronic sleep disorder, and only 50% of people are estimated to get the recommended seven to eight hours of sleep each night. It is further estimated that sleep deprivation and its associated medical and social costs (loss of productivity, industrial accidents, etc.) exceed $150 billion per year. Excessive sleepiness can deteriorate quality of life and is a major cause of morbidity and mortality due to its role in industrial and transportation accidents. Sleepiness further has undesirable effects on motor vehicle driving, employment, higher earning and job promotion opportunities, education, recreation, and personal life.

Primary sleep disorders affect approximately 50 million Americans of all ages and include narcolepsy, restless legs/periodic leg movement, insomnia, and most commonly, sleep apnea. Sleep apnea is defined as the cessation of breathing during sleep. Hundreds of episodes of apnea may occur in one night, lasting 10 seconds or longer, thereby disrupting sleep. The three major types of sleep apnea are obstructive sleep apnea (OSA), central sleep apnea (CSA), and complex sleep apnea (CompSA). The prevalence of OSA in society is comparable with diabetes, asthma, and the lifetime risk of colon cancer. OSA is grossly under diagnosed; an estimated 80-90% of persons afflicted have not received a clinical diagnosis. OSA is characterized by repetitive pauses in breathing during sleep due to the obstruction and/or collapse of the upper airways, usually accompanied by a reduction in blood oxygen saturation. Despite obstructions, respiratory effort continues during the episodes of OSA. In contrast to OSA, where the central nervous system continues to drive respiratory effort but a physical blockage prevents inhalation of oxygen, CSA is a neurological condition resulting in the cessation of respiratory effort during sleep.

Although the effects of OSA and CSA are highly similar, effective treatment can differ because the physical cause of OSA is very different from the neurological mechanism behind CSA. Because the treatments of OSA and CSA vary substantially, proper diagnosis of the correct type of sleep apnea is critical for an effective treatment. The most common method of treating OSA is the use of positive airway pressure (PAP), generated by a PAP device. PAP treatment is most commonly conducted with the subject wearing an oronasal mask or similar apparatus that is connected to a PAP device via a hose that can deliver the pressurized air generated by the PAP device to the subject's airway. When using a standard PAP device to treat OSA, the positive airway pressure generated by the PAP device acts as a splint, holding the airway open and reducing or removing the obstruction. With continuous positive airway pressure (CPAP) treatment, an optimal pressure is determined by a sleep technician during a titration period in which the positive pressure provided by the CPAP is adjusted until a pressure sufficient to maintain airway patency is found and thus reduces the number of apneic events experienced by the subject being treated. Once the optimal pressure is determined, the device is programmed to consistently provide this pressure, and the patient is sent home.

Slightly more advanced PAP devices automatically adjust the air pressure based on sensory feedback mechanisms built into the device. The sensors measure gas flow, pressure, or other fluid characteristics in the device, mask, or both and adjust the delivered pressure based on various algorithms known in the art. Additionally, these auto-PAP devices predict or detect an apnea event by measuring a subject's exhaled air using similar sensors. The many variations of PAP devices are generally referred to as PAP devices, with specific variations noted where appropriate.

Subjects with CompSA are characterized by the emergence of CSA events after the application of PAP therapy. CompSA can be thought of as a combination of OSA and CSA. Current PAP devices are insufficient for the treatment of CSA or CompSA because the delivered pressure is only able to combat airway obstructions rather than the neurological condition disrupting respiratory effort associated with central sleep apnea. While pressure cannot combat CompSA or CSA, physiologically excess carbon dioxide induces chemoreceptors to signal the nervous system to increase respiratory effort drive. U.S. Pat. No. 7,886,740 to Thomas et al., issued Feb. 15, 2011, adds low concentrations of carbon dioxide from an external $CO_2$ source to the delivered pressurized air from a PAP device and delivers the mixture to a subject. The addition of $CO_2$ from an external source, however, requires additional tubing, machinery (such as a cart), and another point of maintenance for the subject when the $CO_2$ supply is exhausted or machinery fails. Thomas additionally discusses using a variable dead-space mask which would cause the patient to rebreathe his own $CO_2$ that accumulates in the mask. However, these embodiments struggle to control proper $CO_2$ levels in the mask and during inspiration when mixed with air from a PAP device.

It is therefore an object of the present invention to provide an effective means of treating sleep disorders, particularly sleep related breathing disorders by providing $CO_2$ to a subject in controlled quantities. It is another object of the present invention to increase patient comfort and treatment effectiveness by using a subject's exhaled air as a source of $CO_2$, particularly through a rebreathing circuit. It is still another object of the present invention to actively control $CO_2$ concentrations delivered to a subject based on physical properties measured from air in the rebreathing circuit. It is still another object of the present invention to actively control $CO_2$ concentrations delivered to a subject based on physiological signals measured from the subject. It is still another object of the present invention to treat a subject's apnea in a manner predictive of the subject's breathing patterns. It is still another object of the present invention to provide a device and method of controlling levels of CO2 delivered to a subject in the subject's home. It is still another object of the present invention to provide a device and method of controlling levels of CO2 delivered to a subject in a hospital's acute or sub-acute settings, such as for postoperative management of care.

SUMMARY OF THE INVENTION

The present invention pertains to a system, method, and device for treating sleep disorders. The present invention is particularly useful in the delivery of carbon dioxide (CO2) to a subject and in the treatment of sleep apnea. Furthermore, integration of components with various sensors and apparatuses associated therewith and attached thereto preferably complete a rebreathing circuit in the present invention. In various embodiments of the present invention where the above components are integrated as a rebreathing circuit, a subject is the source and recipient of a controlled volume of a specific concentration of carbon dioxide. In such embodiments, treatment of sleep disorders becomes much more efficient and effective.

In certain preferred embodiments of the present invention, a rebreathing circuit is created by capturing a subject's exhaled air, diluting its concentration of carbon dioxide with a dilutive gas such as atmospheric air, pressurizing the mixture to a pressure greater than atmospheric pressure and delivering the diluted and pressurized mixture to the subject. In such embodiments, flow is most preferably unidirectional and controlled via a series of regulatory valves or the like. Regulatory valves may be of many types such as check valves for controlling flow of direction, needle valves for controlling flow rate and volume, and the like. In certain embodiments the regulatory valves are passive while still in other embodiments, the regulatory valves are controlled by a processor, actuator, and the like. A controlling processor preferably controls regulatory valve operation by analyzing signals generated by various sensors attached throughout the rebreathing circuit including those that monitor the subject's breathing and those that monitor air within the rebreathing circuit. Such sensors may include pneumotachographs, acoustic transducers, respiratory plethysmography belts, and the like for monitoring a subject's breathing, airflow and effort. Other sensors may include carbon dioxide sensors, pressure transducers, thermistors, and the like for measuring properties of the exhaled and delivered air. Using these sensors as feedback mechanisms to check against preset pressure ranges, concentration ranges, and the like, the controlling processor can actively control regulatory valves used for mixing and passing air.

Additionally, certain devices of various preferred embodiments of the present invention also comprise LED displays, LCD displays, push buttons, lights, speakers, and similar mechanisms for user interaction. By way of example, in one preferred embodiment, a PAP device of the present invention for delivering pressurized air containing CO2 to a subject comprises an LCD touch screen as a graphical user interface (GUI). The LCD touch screen may be used by a sleep technician or a subject to program various parameters of the present invention, such as treatment period, CO2 concentration, air delivery pressure, and the like. The LCD screen may also alert the subject to various errors, warnings, notifications, and the like. In the present invention, the GUI is preferably controlled by electronics in communication with the processors used to regulate regulatory valves and monitor sensors described above. In still other embodiments, the display used can comprise a display independent of a PAP device, such as the display of a smart cellular phone or other portable user interface. In such embodiments, a connection between the independent display and the PAP device and its associated control systems can be established using wireless communication protocols such as Bluetooth® or IEEE 802.11, or wired connections such as USB. PAP device settings can then be controlled and regulated using the independent display as an input device to the PAP device. If a wireless connection is implemented it is preferable that the connection be secured by encryption, pairing, or other similar means. Also, the independent display device may include software that can properly interface with the PAP device of the present invention in order to program various parameters of the present invention, such as treatment period, CO2 concentration, air delivery pressure, and the like.

A number of embodiments of the present invention are envisioned in this disclosure. The following embodiments are examples of the many embodiments encompassed by the present invention, but do not in any way limit the many other embodiments covered by this disclosure.

In one embodiment, the present invention includes a sleep-related breathing disorder treatment system comprising a capture device for capturing exhaled air from a subject; a positive airway pressure (PAP) device for mixing and pressurizing at least captured exhaled air and a dilutive gas to a pressure that is greater than atmospheric pressure; and a delivery device for delivering the pressurized mixture of at least the captured exhaled air and dilutive gas to the subject, wherein the delivery device completes a rebreathing circuit between at least the PAP device and capture device.

In still another embodiment, the present invention includes a sleep-related breathing disorder treatment system comprising a capture device for capturing exhaled air from a subject; a positive airway pressure (PAP) device for mixing and pressurizing at least captured exhaled air and a dilutive gas to a pressure that is greater than atmospheric pressure; and a delivery device for delivering the pressurized mixture of at least the captured exhaled air and dilutive gas to the subject, wherein the delivery device completes a rebreathing circuit between at least the PAP device and capture device, further comprising at least one sensor for measuring at least one parameter of the subject's breathing during sleep.

In still another embodiment, the present invention includes a sleep-related breathing disorder treatment system comprising a capture device for capturing exhaled air from a subject; a positive airway pressure (PAP) device for mixing and pressurizing at least captured exhaled air and a dilutive gas to a pressure that is greater than atmospheric pressure; and a delivery device for delivering the pressurized mixture of at least the captured exhaled air and dilutive gas to the subject, wherein the delivery device completes a rebreathing circuit between at least the PAP device and capture device, further comprising at least one sensor for measuring at least one parameter of the subject's breathing during sleep wherein analysis of a signal generated by the at least one sensor is used to control the quantities of captured exhaled air and dilutive gas that are mixed in a mixing chamber.

In still another embodiment, the present invention includes a sleep-related breathing disorder treatment system comprising a capture device for capturing exhaled air from a subject; a positive airway pressure (PAP) device for mixing and pressurizing at least captured exhaled air and a dilutive gas to a pressure that is greater than atmospheric pressure; and a delivery device for delivering the pressurized mixture of at least the captured exhaled air and dilutive gas to the subject, wherein the delivery device completes a rebreathing circuit between at least the PAP device and capture device wherein the capture device is a bellows.

In still another embodiment, the present invention includes a sleep-related breathing disorder treatment system comprising a capture device for capturing exhaled air from a subject; a positive airway pressure (PAP) device for mixing and pressurizing at least captured exhaled air and a dilutive gas to a pressure that is greater than atmospheric pressure; and a delivery device for delivering the pressurized mixture of at least the captured exhaled air and dilutive gas to the subject, wherein the delivery device completes a rebreathing circuit between at least the PAP device and capture device wherein the rebreathing circuit between at least the capture device, the PAP device, and the delivery device is arranged so as to cause airflow to proceed from the subject to the capture device, to the PAP device, and back to the subject via the delivery device.

In still another embodiment, the present invention includes a sleep-related breathing disorder treatment system comprising a capture device for capturing exhaled air from a subject; a positive airway pressure (PAP) device for mixing and pressurizing at least captured exhaled air and a dilutive gas to a pressure that is greater than atmospheric pressure; and a delivery device for delivering the pressurized mixture of at least the captured exhaled air and dilutive gas to the subject, wherein the delivery device completes a rebreathing circuit between at least the PAP device and capture device wherein the sleep-related breathing disorder treatment system is a system for treating sleep apnea.

In still another embodiment, the present invention includes a sleep-related breathing disorder treatment system comprising a capture device for capturing exhaled air from a subject; a positive airway pressure (PAP) device for mixing and pressurizing at least captured exhaled air and a dilutive gas to a pressure that is greater than atmospheric pressure; and a delivery device for delivering the pressurized mixture of at least the captured exhaled air and dilutive gas to the subject, wherein the delivery device completes a rebreathing circuit between at least the PAP device and capture device wherein the captured exhaled air and dilutive gas are mixed to produce a mixture that contains a concentration of carbon dioxide that is greater than about 0.5%.

In yet another embodiment, the present invention includes a method for treating sleep-related breathing disorders comprising the steps of capturing exhaled air from a subject; mixing at least the captured exhaled air and a dilutive gas in controlled quantities; and providing the mixture of at least captured exhaled air and dilutive gas to the subject using a positive airway pressure (PAP) device to complete a rebreathing circuit.

In still yet another embodiment, the present invention includes a method for treating sleep-related breathing disorders comprising the steps of capturing exhaled air from a subject; mixing at least the captured exhaled air and a dilutive gas in controlled quantities; and providing the mixture of at least captured exhaled air and dilutive gas to the subject using a positive airway pressure (PAP) device to complete a rebreathing circuit wherein the method further comprises measuring at least one parameter of the subject's breathing with at least one sensor.

In still yet another embodiment, the present invention includes a method for treating sleep-related breathing disorders comprising the steps of capturing exhaled air from a subject; mixing at least the captured exhaled air and a dilutive gas in controlled quantities; and providing the mixture of at least captured exhaled air and dilutive gas to the subject using a positive airway pressure (PAP) device to complete a rebreathing circuit wherein mixing of at least captured exhaled air and atmospheric air is controlled at least in part by a processor capable of analyzing signals generated by the at least one sensor.

In still yet another embodiment, the present invention includes a method for treating sleep-related breathing disorders comprising the steps of capturing exhaled air from a subject; mixing at least the captured exhaled air and a dilutive gas in controlled quantities; and providing the mixture of at least captured exhaled air and dilutive gas to the subject using a positive airway pressure (PAP) device to complete a rebreathing circuit wherein the mixing of at least captured exhaled air and dilutive gas is controlled according to at least one predetermined setting.

In still yet another embodiment, the present invention includes a method for treating sleep-related breathing disorders comprising the steps of capturing exhaled air from a subject; mixing at least the captured exhaled air and a dilutive gas in controlled quantities; and providing the mixture of at least captured exhaled air and dilutive gas to the subject using a positive airway pressure (PAP) device to complete a rebreathing circuit wherein the sleep-related breathing disorder is sleep apnea.

In still yet another embodiment, the present invention includes a method for treating sleep-related breathing disorders comprising the steps of capturing exhaled air from a subject; mixing at least the captured exhaled air and a dilutive gas in controlled quantities; and providing the mixture of at least captured exhaled air and dilutive gas to the subject using a positive airway pressure (PAP) device to complete a rebreathing circuit wherein the step of mixing produces a mixture of at least exhaled air and dilutive gas that contains a concentration of carbon dioxide that is greater than about 0.5%.

In still yet another embodiment, the present invention includes a positive airway pressure (PAP) device comprising a mixing chamber for mixing at least a subject's exhaled air and a dilutive gas in controlled quantities; a pressurized air generator; a one-way input valve for passing the subject's exhaled air into the mixing chamber; and a one-way output valve for passing of a mixture of at least the subject's exhaled air and a dilutive gas out of the mixing chamber using at least in part the source of pressurized air.

In still yet another embodiment, the present invention includes A positive airway pressure (PAP) device comprising a mixing chamber for mixing at least a subject's exhaled air and a dilutive gas in controlled quantities; a pressurized air generator; a one-way input valve for passing the subject's exhaled air into the mixing chamber; and a one-way output valve for passing of a mixture of at least the subject's exhaled air and a dilutive gas out of the mixing chamber using at least in part the source of pressurized air wherein the one-way input valve is connected to a capture device for capturing exhaled air from the subject and the one-way output valve is connected to a delivery device for delivering a mixture of at least the captured exhaled air and the dilutive gas to the subject.

In still yet another embodiment, the present invention includes A positive airway pressure (PAP) device comprising a mixing chamber for mixing at least a subject's exhaled air and a dilutive gas in controlled quantities; a pressurized air generator; a one-way input valve for passing the subject's exhaled air into the mixing chamber; and a one-way output valve for passing of a mixture of at least the subject's exhaled air and a dilutive gas out of the mixing chamber using at least in part the source of pressurized air wherein the capture device and the delivery device are connected to a single, multifunctional mask.

In still yet another embodiment, the present invention includes A positive airway pressure (PAP) device comprising a mixing chamber for mixing at least a subject's exhaled air and a dilutive gas in controlled quantities; a pressurized air generator; a one-way input valve for passing the subject's exhaled air into the mixing chamber; and a one-way output valve for passing of a mixture of at least the subject's exhaled air and a dilutive gas out of the mixing chamber using at least in part the source of pressurized air, further comprising at least one sensor and at least one processor to actively control mixing of the subject's exhaled air and the dilutive gas in response to changes in the subject's breathing.

In still yet another embodiment, the present invention includes A positive airway pressure (PAP) device comprising a mixing chamber for mixing at least a subject's exhaled air and a dilutive gas in controlled quantities; a pressurized air generator; a one-way input valve for passing the subject's exhaled air into the mixing chamber; and a one-way output valve for passing of a mixture of at least the subject's exhaled air and a dilutive gas out of the mixing chamber using at least in part the source of pressurized air, further comprising at least one sensor and at least one processor to actively control mixing of the subject's exhaled air and the dilutive gas according to at least one predetermined setting.

In still yet another embodiment, the present invention includes A positive airway pressure (PAP) device comprising a mixing chamber for mixing at least a subject's exhaled air and a dilutive gas in controlled quantities; a pressurized air generator; a one-way input valve for passing the subject's exhaled air into the mixing chamber; and a one-way output valve for passing of a mixture of at least the subject's exhaled air and a dilutive gas out of the mixing chamber using at least in part the source of pressurized air, further comprising a display for displaying the amount of carbon dioxide included in the mixture of at least the subject's exhaled air and atmospheric air.

In still yet another embodiment, the present invention includes A positive airway pressure (PAP) device comprising a mixing chamber for mixing at least a subject's exhaled air and a dilutive gas in controlled quantities; a pressurized air generator; a one-way input valve for passing the subject's exhaled air into the mixing chamber; and a one-way output valve for passing of a mixture of at least the subject's exhaled air and a dilutive gas out of the mixing chamber using at least in part the source of pressurized air wherein the subject's exhaled air and the dilutive gas are mixed to produce a mixture that contains a concentration of carbon dioxide that is greater than about 0.5%.

It is to be understood that the foregoing summary and general description and the following brief and detailed descriptions and accompanying figures are merely exemplary of the present invention, and are only intended to provide an overview or framework for understanding the nature and character of the invention as it is claimed.

BRIEF DESCRIPTION OF THE DRAWINGS

FIG. 10a Illustration of one embodiment of a flow-based regulatory valve for use in the present invention where delivery air is flowing from a positive airway pressure device to a subject.

FIG. 10b Illustration of one embodiment of a flow-based regulatory valve for use in the present invention where exhaled air is captured away from the positive airway pressure device.

FIG. 11a Illustration of a second embodiment of a flow-based regulatory valve for use in the present invention where delivery air is flowing from the positive airway pressure device to the subject.

FIG. 11b Illustration of a second embodiment of a flow-based regulatory valve for use in the present invention where exhaled air is captured away from the positive airway pressure device.

DETAILED DESCRIPTION OF THE INVENTION

Figure 1:
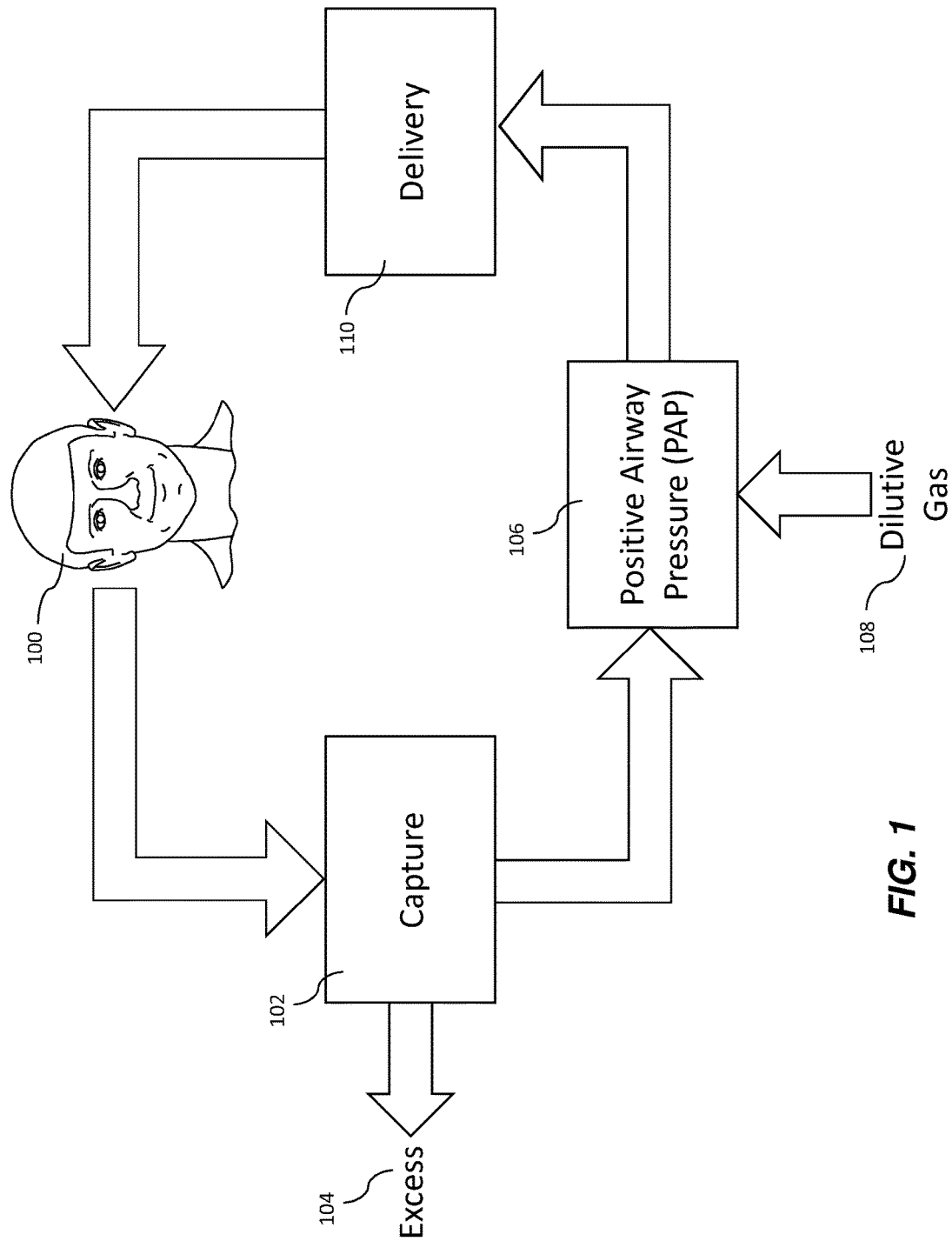
FIG. 1 Diagram illustrating the path of airflow in a rebreathing circuit of the present invention in its simplest form.

The present invention pertains to a system, method, and device for treating sleep disorders. The present invention is particularly useful in the delivery of carbon dioxide ($CO_2$) to a subject and in the treatment of sleep apnea. Furthermore, integration of three primary components with various sensors and apparatuses associated therewith and attached thereto preferably complete a rebreathing circuit in the present invention. In various embodiments of the present invention where the above components are integrated as a rebreathing circuit, a subject is the source and recipient of a controlled volume of a specific or controlled concentration of carbon dioxide. In such embodiments, with the addition of $CO2$, treatment of sleep disorders becomes much more efficient and effective. While the following detailed description describes preferred embodiments of a rebreathing circuit for delivering $CO2$, it is to be understood that these embodiments are merely exemplary and are not inclusive of every system, method, or device included within the scope of the present invention.

The first primary component of the present invention is a device for capturing exhaled air from a subject, hereinafter referred to as a capture device. For purposes of this invention, a capture device means any device that is capable of capturing, retaining, and releasing a volume of air, hereinafter captured air, that has been exhaled by a subject. For example, this may be a device of fixed volume, such as a hose, multi-lumened hose, tube, or the like; or a device of variable volume, such as a bellows that expands and contracts as air is added to and removed from the capture device. Preferably, the capture device is able to capture and at least temporarily store between 100 mL and 5000 mL of a subject's exhaled air. More preferably, the capture device is able to capture and at least temporarily store between 150 mL and 3000 mL of a subject's exhaled air. Still more preferably, the capture device is able to capture and at least temporarily store between 200 mL and 2000 mL of a subject's exhaled air. Even more preferably, the capture device is able to capture and at least temporarily store between 250 mL and 1500 mL of a subject's exhaled air. Still even more preferably, the capture device is able to capture and at least temporarily store between 250 mL and 1000 mL of a subject's exhaled air. In certain preferred embodiments, the capture device preferably has at least two openings for the flow of air: one opening proximal to a subject for capturing a subject's exhaled air and one opening distal to a subject for releasing the retained air so as to create a path within the capture device that a subject's exhaled air may travel through by being captured in the proximal opening of the capture device and being released through the distal opening of the capture device. For purposes of the present invention, the terms proximal and distal will be used hereinafter as being relative to a subject unless otherwise noted. In other words, proximal as used hereinafter means proximal to a subject using the device disclosed herein, while distal means distal to a subject using the device of the present invention. It will further be understood that distal and proximal are used herein as relative terms, meaning that for something to be proximal it needs only to be nearer to the subject than something distal. In order to capture the greatest percentage of a subject's exhaled air, the proximal opening of the capture device of certain preferred embodiments may be fitted to a subject's nose, mouth, or both in the form of a nasal cannula, mouthpiece, oronasal mask, or the like.

The second primary component of the present invention is a device for delivering air to a subject, hereinafter referred to as a delivery device. Similar to the capture device, a delivery device includes any device which is capable of accepting, retaining, and releasing a volume of air, hereinafter delivery air, for a subject to inhale. Like the capture device, the delivery device can take many forms such as a fixed volume hose, multi-lumened hose, tube, or the like; or a device of variable volume, such as a bellows that expands and contracts as air is added to and removed from the delivery device, or the like. Preferably, the delivery device has a volume of between 100 mL and 5000 mL. More preferably, the delivery device has a volume of between 150 mL and 3000 mL. Still more preferably, the delivery device has a volume of between 200 mL and 2000 mL. Even more preferably, the delivery device has a volume of between 250 mL and 1500 mL. Still even more preferably, the delivery device has a volume of between 250 mL and 1000 mL. Additionally, in certain preferred embodiments, the delivery device preferably has at least two openings: one proximal to a subject for delivering air for a subject to inhale and one distal to a subject for accepting the air to deliver, so as to create a path within the delivery device that delivery air may travel through by entering at the distal opening of the delivery device and exiting through the proximal opening of the delivery device. In order for a subject to inhale the greatest amount of delivered air, the proximal opening of the delivery device of certain preferred embodiments is fitted to a subject's nose, mouth, or both in the form of a nasal cannula, mouthpiece, oronasal mask, or the like. While a limited number of embodiments are described here, it will be clear to one of ordinary skill in the art that the delivery device may take many forms.

In certain embodiments, the ends of the capture device and the delivery device that are proximal to a subject may be the same or connected at a common point of connection. For example, a subject may wear a single oronasal mask covering both the subject's nose and mouth, to which the proximal ends of both the capture device and delivery device are preferably connected via one-way pressure actuated valves. Therefore, as the subject exhales, the subject's exhaled air enters the oronasal mask causing the oronasal mask to fill with exhaled air and the air pressure inside the oronasal mask to rise. At the critical pressure for the one-way valve on the proximal end of the capture device, the valve opens allowing exhaled air to exit the oronasal mask, pass through the proximal opening, and be captured by the capture device. Similarly, delivery air in the delivery device may be delivered by passing through a valve at the proximal opening of the delivery device connected to the oronasal mask and be inhaled by the subject once inside the oronasal mask. Valves may also be actuated based on flow direction or by a servo, solenoid, or the like, that is controlled by a controlling processor programmed to synchronize valve opening and closing with a subject's breathing patterns to minimize potential mixing of exhaled air and delivery air within the oronasal mask. In various embodiments, an oronasal mask may also have vents to release excess exhaled or delivered air and maintain a desired pressure within the mask. Masks and other attachments to the proximal ends of the capture and delivery devices, such as nasal cannulas, oral-only masks, nasal-only masks, and other similar devices, preferably further include an apparatus for securely attaching the mask or other attachment to a subject's head. This attachment to the head may be one or a combination of any number of mechanisms known to those skilled in the art such as a strap, set of straps, chinstrap, head band, adhesive, and the like. While the aforementioned descriptions are exemplary of certain embodiments, it is to be understood that many other types of control mechanisms such as electrically controlled servos for the one-way valves, feedback sensors, and the like; valves such as needle valves, ball valves, flow-based valves, and the like; and combinations of proximal openings such as an independent mouthpiece and nasal cannula, independent nasal and mouth masks, combined mouthpieces, and the like may also be used in the present invention.

The third primary component of the present invention is a device for pressurizing air for delivery to a subject. In certain preferred embodiments of the present invention, the device for pressurizing air for delivery to a subject is a positive airway pressure (PAP) device. However, in still other preferred embodiments of the present invention, this device can be a continuous positive airway pressure (CPAP) device, a bi-level positive airway pressure device (BiPAP), standard and adaptive ventilators, or the like, that can preferably generate a pressure greater than atmospheric pressure. For purposes of the present invention, any device for pressurizing air for delivery to a subject will be referred to generally as a PAP device. Preferably, the PAP device of the present invention can generate pressures of at least 1 cm H20. More preferably, the PAP device can generate pressures of at least 5 cm H20. Even more preferably, the PAP device can generate pressures of at least 10 cm H20. Still more preferably, the PAP device can generate pressures of at least 20 cm H20. Still even more preferably, the PAP device can generate pressures of at least 30 cm H20. Still even more preferably, the PAP device can generate pressures of at least 40 cm H20. The PAP device of the present invention preferably connects to the distal opening of the capture device and to the distal opening of the delivery device so as to complete a circuit for a subject's exhaled air to pass through and at least in part be rebreathed by the subject. Furthermore, the PAP device of the present invention preferably acts as a delivery force by moving air from the capture device to the delivery device and helping to dilute the concentration of carbon dioxide in the captured air as described below.

Unlike U.S. Pat. No. 7,886,740 to Thomas et al., issued Feb. 15, 2011, herein incorporated by reference, which in general uses an external source of dilutive gas, the concentration of carbon dioxide ($CO_2$) in a subject's exhaled air in the capture device is preferably diluted with ambient atmospheric air prior to delivery back to the subject via the delivery device. It will be noted, however, that other gasses such as medical grade oxygen, nitrogen, or gas mixtures, including those which themselves contain carbon dioxide, may be used as long as the concentration of $CO_2$ in the gas mixture is less than that in the captured exhaled air and the concentrations of each gas in the air delivered to a subject remains within standard physiologically safe ranges as known to those skilled in the art. The dilutive gasses for mixing with the captured air are described earlier in the specification and are preferably contained within a containment device. Such containment devices may be external or internal to the PAP device depending on the location of mixing. The containment device is preferably air tight. More preferably the containment device is a canister. Alternatively, the containment device may preferably be a pressurized canister. It should also be noted as mentioned earlier that because of potential mixing between a subject's exhaled air and delivery air in a mask, captured air may already be partially diluted while it is retained in the capture device. Therefore, in some instances there is a critical distinction between captured air and exhaled air while in others they are the same. Because of this potential mixing between exhaled air and delivery air or other mixing effects depending on the device configuration, it may sometimes be necessary to supplement the $CO_2$ concentration of captured air. Therefore, in certain embodiments, supplemental concentrated $CO_2$ or a supplemental gas mixture that contains a greater concentration of carbon dioxide than the desired $CO_2$ delivery concentration may be used to increase the concentration of $CO_2$ of the captured air. This supplemental $CO_2$ can be provided, for example, using canisters of concentrated pressurized $CO_2$ or using a $CO_2$ concentrator. If a $CO_2$ concentrator is used, the $CO_2$ concentrator preferably functions to accept input air having a certain concentration of $CO_2$ and then remove other gasses from the input air resulting in an output air with a higher concentration of $CO_2$. The $CO_2$ concentrator may use zeolite materials, catalysts and other materials known to those of ordinary skill in the art in order to provide output air that includes an increased concentration of $CO_2$. As with the dilutive gas, the gases and their concentrations of the supplemental gas mixture is preferably maintained at physiologically safe levels as known to those of ordinary skill in the art. Gasses with high concentrations of $CO_2$ may also be used to increase $CO_2$ concentrations in the delivery air provided proper safeguards are used that would prevent the delivery air from exceeding physiologically safe concentrations of $CO_2$. Furthermore, the supplemental concentrated $CO_2$ or supplemental gas mixture is preferably contained within a containment device located within the PAP device, however, it may be external to the PAP device as well depending on the mixing location.

In certain embodiments of the present invention, the dilutive gas or supplemental gas is mixed with the captured air by the PAP device due to turbulence created by a fan, pump, or similar action in a pressurized air generator of the PAP device. In other embodiments, however, there may be a separate mixing chamber within the PAP device, connected between the capture device and the PAP device, or connected between the PAP device and delivery device. In these embodiments, the mixing chamber preferably contains a number of baffles to increase turbulence and thereby increase the mixing efficiency of the captured air and the dilutive gas or supplemental gas. In certain other embodiments where the mixing chamber is external to the PAP device, the mixing chamber is preferably located between the capture device and PAP device or the PAP device and delivery device. When located between the capture device and the PAP device, the mixing chamber preferably takes in dilutive gas or supplemental gas and captured air, and outputs a mixture of the two to the PAP device. When located between the PAP device and delivery device, the mixing chamber preferably takes in dilutive gas or supplemental gas and the pressurized captured air output from the PAP device, and outputs a mixture of the two to the delivery device. Furthermore, the mixing chamber preferably still contains a number of baffles or other elements in these embodiments, regardless of its location, to create turbulence thereby increasing mixing efficiency.

Furthermore, in certain preferred embodiments, moisture is added to the mixture to increase patient comfort while using the device. For example, U.S. patent application Ser. No. 11/505,204, filed Aug. 16, 2006, herein incorporated by reference, describes a humidifier integrated with a PAP device as a way to increase patient comfort and decrease side effects of PAP devices by humidifying air delivered from a PAP device to a subject. While the actual concentration of carbon dioxide in a subject's exhaled air varies, it generally remains between five and seven percent while the subject is sleeping; likewise, the concentration of carbon dioxide to be delivered is variable between subjects, but is generally about one percent. Preferably, the concentration of carbon dioxide that can be delivered to a subject using the PAP device is between 0.8 percent and 1.2 percent. More preferably, the concentration of carbon dioxide that can be delivered to a subject is between 0.5 percent and 1.5 percent. Even more preferably, the concentration of carbon dioxide that can be delivered to a subject is between 0.25 percent and 2 percent. Still more preferably, the concentration of carbon dioxide that can be delivered to a subject is between 0.1 percent and 2.5 percent. Still even more preferably, the concentration of carbon dioxide that can be delivered to a subject is between 0.01 percent and 5.0 percent. Preferably, the accuracy of the concentration of delivered carbon dioxide is within 75 percent of the desired concentration. More preferably, the accuracy of the concentration of delivered carbon dioxide is within 50 percent of the desired concentration. Even more preferably, the accuracy of the concentration of delivered carbon dioxide is within 20 percent of the desired concentration. Still more preferably, the accuracy of the concentration of delivered carbon dioxide is within 10 percent of the desired concentration. Still even more preferably, the accuracy of the concentration of delivered carbon dioxide is within 5 percent of the desired concentration. Still even more preferably, the accuracy of the concentration of delivered carbon dioxide is less than 1 percent of the desired concentration.

In certain preferred embodiments, a rebreathing circuit is completed by capturing a subject's exhaled air at the proximal opening of the capture device, mixing it with dilutive gas to decrease the concentration of carbon dioxide in the captured air, pressurizing the mixture to a pressure greater than atmospheric pressure and delivering the diluted and pressurized air to the subject at the proximal opening of the delivery device. Flow is most preferably unidirectional from a subject to the capture device, to the PAP device, to the delivery device, and finally back to the subject. Preferably flow is also controlled via a series of regulatory valves. Regulatory valves may be of many types such as check valves for controlling flow of direction, needle valves for controlling flow rate and volume, and the like. In certain embodiments the regulatory valves are passive while still in other embodiments, the regulatory valves are controlled by a processor. A controlling processor preferably controls regulatory valve operation by analyzing signals generated by various sensors attached throughout the rebreathing circuit and then operating a servo, solenoid, actuator, or the like attached to the valve, thereby resulting in the desired physical valve operation. Sensors used during valve operation may include pneumotachographs, acoustic transducers, pressure transducers, thermistors, respiratory plethysmography belts, and the like for monitoring a subject's breathing airflow and effort. Sensors for measuring properties of the subject's exhaled air and the delivery air may also include carbon dioxide sensors, thermistors, oxygen sensors, pressure transducers, and the like. Using these sensors as part of feedback mechanisms to check against preset pressure ranges, concentration ranges, and the like, the processor can regulate valves used for mixing and delivering air to a subject.

Various embodiments of the PAP device also preferably include control electronics for at least controlling regulatory valves at the proximal and distal ends of the capture and delivery devices and controlling a graphical user interface. Control electronics are preferably also responsible for controlling regulatory valves at an input for dilutive gas or supplemental gas on the PAP device. In these embodiments, processors are programmed to send control signals to servos, solenoids, actuators, and the like under programmed conditions which in turn mechanically operate the regulatory valves upon receiving proper signals from the processor. In certain embodiments, processors receive feedback signals from sensors monitoring air such as CO2 sensors, pressure sensors, and the like; and sensors monitoring a subject's breathing such as respiratory plethysmography belts, pneumotachographs, and the like. In these embodiments, processors are programmed to interpret signals from the above sensors before determining the appropriate action for each regulatory valve.

In certain other embodiments, the PAP device may comprise a user interface further comprised of LED displays, LCD displays, push buttons, speakers, and the like. The user interface, hereinafter referred to as a graphical user interface (GUI) although it may contain auditory components, is preferably designed to allow a sleep technician or subject to manually control the function of the control processors and therefore the regulatory valves, display data from sensors, alert a technician or subject to warnings or errors, and the like. Due to the relationship between the GUI and the functionality of the PAP device of the present invention, the GUI is preferably controlled by processors among the same electronics as those that control the regulatory valves previously described. This relationship preferably also serves a self-diagnostic function such that the regulatory valve control processors may relay hardware error signals to the GUI control processors which in turn signals the GUI to alert the user of any errors within the PAP device. Furthermore, additional hardware such as analog to digital or digital to analog converters, filters, and the like may also be incorporated within the PAP control electronics connecting the processors, sensors, and GUI. In certain embodiments where the mixing chamber is external from the PAP device, the mixing chamber preferably also has control electronics and a GUI separate from those of the PAP device. In this way, a subject may use a currently owned PAP device and simply attach a mixing chamber to create a rebreathing circuit of the present invention. Therefore, the control electronics and GUI of the external mixing chamber control, in part, the regulatory valves of the mixing chamber and concentrations of CO2 used for mixing captured air. The control electronics and GUI of the PAP device then control positive airway pressure output as they normally would. When used together, the subject receives delivery air with a concentration of carbon dioxide at least partially containing his own exhaled air just as he would if the mixing chamber were a part of the PAP device.

The hardware, firmware, and software of the control electronics in certain embodiments preferably contain adaptive algorithms for controlling regulatory valves as a subject's breathing patterns change, concentrations of carbon dioxide in captured air and delivery change, and volumes of captured and delivery air change. These algorithms preferably take into account various sensors located throughout a rebreathing circuit of the present invention as a means of feedback control. Sensors may be located in the capture device, delivery device, PAP device, an oronasal mask, mixing chamber, or the like. Sensors preferably include those already described such as pneumotachographs, acoustic transducers, respiratory plethysmography belts, and the like for monitoring a subject's breathing, airflow and effort. Other sensors may include carbon dioxide sensors, pressure transducers, thermistors, and the like for measuring properties of the exhaled and delivered air. The control electronics can be for example a proportional-integral-derivative (PID) controller, an adaptive predictive controller, or an adaptive predictive feedback controller. The control electronics of the present invention are preferably part of a closed loop control system. The control electronics can be used to monitor and control captured air, monitor and control delivery air, and interact with a user, or monitor breathing patters of a subject. One of the sensors previously described in this specification preferably transmits a signal to the control electronics through electrical connection. The control electronics process the signal(s) to determine, through mathematical modeling, the concentrations of CO2 throughout the rebreathing circuit, pressures throughout the rebreathing circuit, a subject's breathing patterns, and the current state of the GUI and user inputs. It is the predictive ability of the control electronics which provides for this function and expands this system from being merely responsive. This is especially advantageous for dynamic systems which are nonlinear, time varying, and operate in challenging environments such as the one of the present invention where a subject's exhaled air and breathing patterns vary over time during sleep. According to the mathematical modeling abilities of the control electronics, the control electronics preferably operate the regulatory valves already described in order to control flow and pressure of air throughout the rebreathing circuit. The control electronics operate the regulatory valves by sending electrical signals to actuators, solenoids, servos, or the like which in turn mechanically operate each regulatory valve. The control electronics preferably also produce an output signal to a monitor, recorder, alarm and/or any peripheral device for alarming, monitoring, such as a GUI previously described to alert any user of the current state of the system of the present invention.

In one preferred embodiment, the PAP device is in the form of a continuous positive airway pressure (CPAP) device and a subject wears an oronasal mask connected to the proximal ends of both the capture and delivery devices. The distal ends of the capture and delivery devices are connected to the CPAP. In this preferred embodiment, the CPAP works by continually supplying positive pressure air, that is, greater than atmospheric pressure, through the delivery device during every phase of a subject's breathing. Due to the continuous supply of positive pressure air by the CPAP, air is continually forced into the distal opening of the delivery device, out the proximal opening of the delivery device, and into the oronasal mask. When the subject is not inspiring, the delivery air will be forced through the proximal end of the capture device and into the capture device. Therefore, as the subject exhales, the capture device will not necessarily contain air with a uniform concentration of carbon dioxide due to the nonuniform capture of delivery air and the subject's exhaled air. Thus, mixing of air by the CPAP must be regulated in order to generate the desired concentration of carbon dioxide in the mixed air. In other words, the first volume of air to be released through the distal end of the capture device and into the CPAP will have a CO2 concentration equal to that of the delivery air; however, after that segment of the capture device has been bled, the next volume of air to be released through the distal end of the capture device and into the CPAP will have a CO2 concentration equal to that of the subject's exhaled air. Properly controlled vents or valves and CO2 sensors may help resolve this issue. For example, the flow-based regulatory valves shown in FIGS. 10a and 10b; 11a and 11b; and 12, and described in more detail below, illustrate two embodiments of valves that may be used to limit or prevent a subject's exhaled air from mixing with delivery air from a CPAP device. Similar to shuttle valves, these flow-based valves contain three ports and allow for two directions of flow: (1) for delivery air from a CPAP (or similar device) to the subject, and (2) for exhaled air from the subject to a capture device. Additionally, respiratory effort and airflow sensors may be used to regulate mixing and delivery based on the subject's breathing phases and thus more accurately calculate concentrations of CO2 throughout the capture device. Using these and/or similar sensors a processor preferably controls valves and vents for mixing, delivering, and capturing air by controlling attached servos, actuators, solenoids, and the like, with at least the above and similar issues in mind.

Turning now to a description of the figures, FIG. 1 illustrates the path of airflow in a rebreathing circuit of the present invention in its simplest form. A subject 100 initially exhales air which is captured 102 by a capture device. In various embodiments, the capture device preferably releases excess air 104 which may be the result of over expiration, overflow or leak from the delivery device, contamination from fresh outside air, or the like. Release preferably occurs through pressure sensitive valves, regulatory valves, or the like. Airflow continues to a positive airway pressure (PAP) device 106 where the concentration of carbon dioxide in the exhaled air is, if necessary, diluted, preferably by dilutive gas 108, to a concentration of about one percent. The exact concentration, however, is variable between subjects and determined by preset values and/or feedback mechanisms. As previously described, the PAP device 106 can mix a subject's captured exhaled air with dilutive gas 108, which may include fresh air, medical grade oxygen, and the like, in an external mixing chamber or within an internal mixing chamber inside the PAP device 106. The pressure generated by the PAP device 106 is preferably greater than atmospheric pressure. The pressurized mixed air then leaves the PAP device 106 and is delivered 110 to the subject 100 by a delivery device to complete the rebreathing circuit. Preferably, the subject 100 wears an oronasal mask attached to the subject's head by a head strap and connected to the proximal ends of both the capture and delivery devices; however, the rebreathing circuit may in certain embodiments be effectively completed with separate masks (e.g. separate oral mask and separate nasal mask as opposed to a single oronasal mask) on the proximal ends of the capture and delivery devices and the subject 100.

Figure 2:
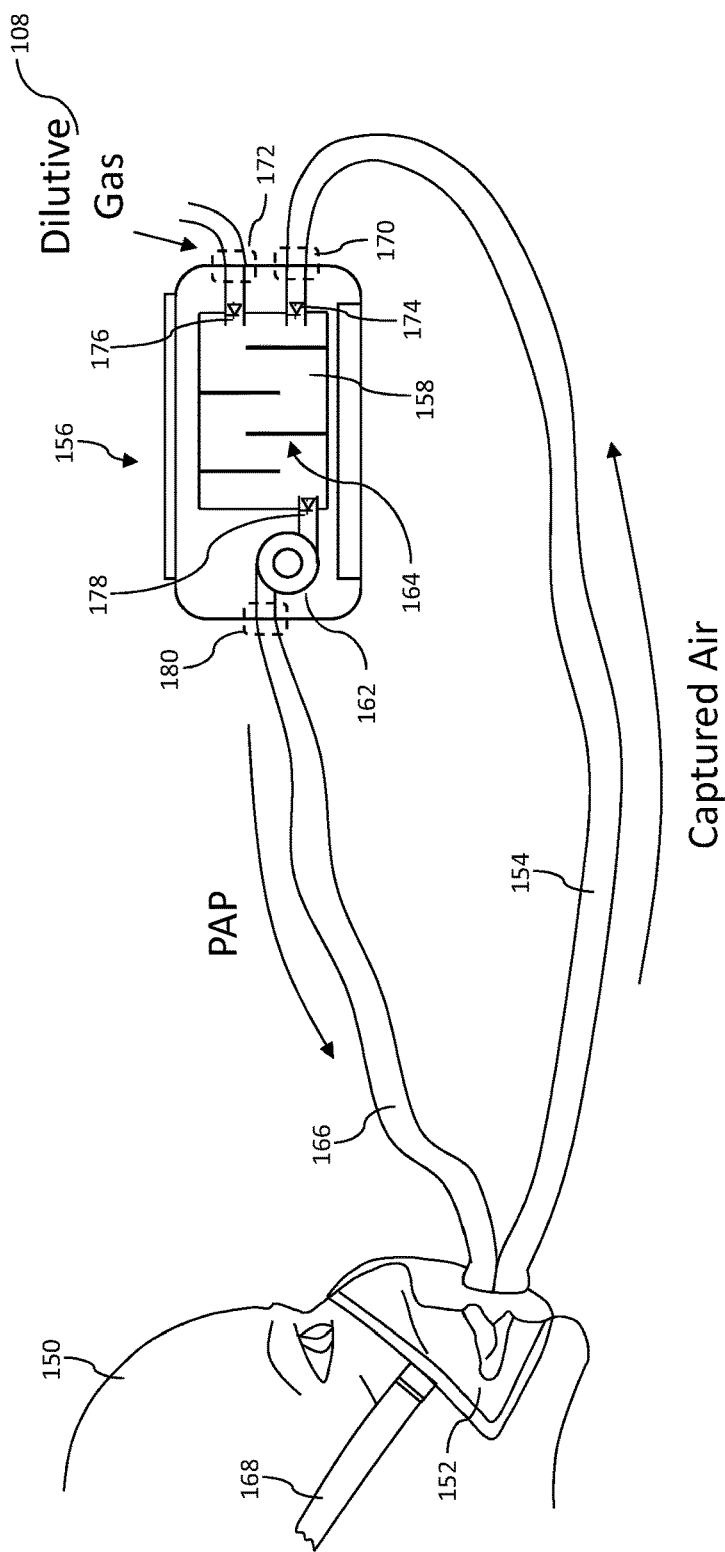
FIG. 2 Diagram illustrating a rebreathing circuit as it would be applied to a subject with a mask, tubes, and positive airway pressure device.

FIG. 2 expands on FIG. 1, illustrating a potential rebreathing circuit as it may be formed in certain embodiments of the present invention with a subject wearing an oronasal mask, air hoses, and a positive airway pressure device. In the preferred embodiment of FIG. 2, a subject 150 breathes into an oronasal mask 152 that is held on the subject's 150 head by an elastic strap 168 around the subject's 150 head. The oronasal mask 152 preferably contains two connections for the proximal ends of the capture and delivery devices. These connections preferably contain one-way valves, flow-based valves, or other regulatory valves known to those skilled in the art to regulate air flow in such a way that exhaled air can only be captured by the air capture hose 154 of the capture device, mixed air can only be delivered by the delivery air hose 166 of the delivery device, and there is no backflow in either air hose. Air preferably flows as illustrated by the arrows shown in FIG. 2. The oronasal mask 152 may also have vents (not shown) to release excess air if pressure inside the oronasal mask 152 is too high, thereby increasing subject comfort. Both the air capture hose 154 and the air delivery hose 166 are preferably made of a lightweight flexible material to decrease interference with the subject 150 while sleeping, but rigid enough to prevent kinks that may stop airflow or drastically increase pressure in the rebreathing circuit. The air hose material is also most preferably impermeable to oxygen, nitrogen, carbon dioxide, hydrogen, and helium, and other atmospheric gasses.

The air capture hose 154 is connected at its distal end to PAP device 156 through one of two input ports 170, 172 on the PAP device 156. In the embodiment of FIG. 2, the second input port 172 of the PAP device 156 is meant to draw dilutive gas 108 into the PAP device 156. In certain embodiments, the second input 172 on the PAP device 156 uses ambient air as a dilutive gas, however, in certain other embodiments, the second input port 172 on the PAP device 156 may be connected to sources of other dilutive gas such as a medical grade oxygen tank, nitrogen tank, medical grade carbon dioxide, or the like. Inside the PAP device 156, each input port 170, 172 is connected to a mixing chamber 158 via regulatory valves 174, 176. While regulatory valves 174, 176 are illustrated in FIG. 2 as incorporated in the PAP device 156, these valves could also just as easily be located in the air capture hose 154 or the oronasal mask 152. Furthermore, in certain embodiments of the present invention a single valve, can be used in place of the two separate regulatory valves 174, 176 illustrated in FIG. 2. The regulatory valves 174, 176 are preferably controlled to regulate the volumes of air from the air capture hose 154, and dilutive gas 108 entering the mixing chamber 158. Regulating volumes of air that enter the mixing chamber 158 allows the desired concentration of carbon dioxide to be reached during mixing. The output of the mixing chamber 158 is connected to a pressurized air generator 162 via another regulatory valve 178 to control output to the air delivery hose 166. The pressurized air generator 162 pressurizes air leaving the mixing chamber 158 to a pressure greater than atmospheric pressure as well as helps pull air into and through the mixing chamber 158 as a result of a pressure gradient when the regulatory valves 174, 176, 178 are open. The mixing chamber 158 preferably also contains a series of baffles 164 to create turbulence and thus help in mixing air from the air capture hose 154 with dilutive gas 108 as they flow through the mixing chamber 158. The output port 180 of the PAP device 156 is connected to the delivery device at the distal end of the air delivery hose 166 as previously described such that pressurized air is preferably forced into and through the air delivery hose 166 and eventually into the oronasal mask 152 connected at the proximal end of the air delivery hose where it can then be inhaled by the subject 150.

Figure 3:
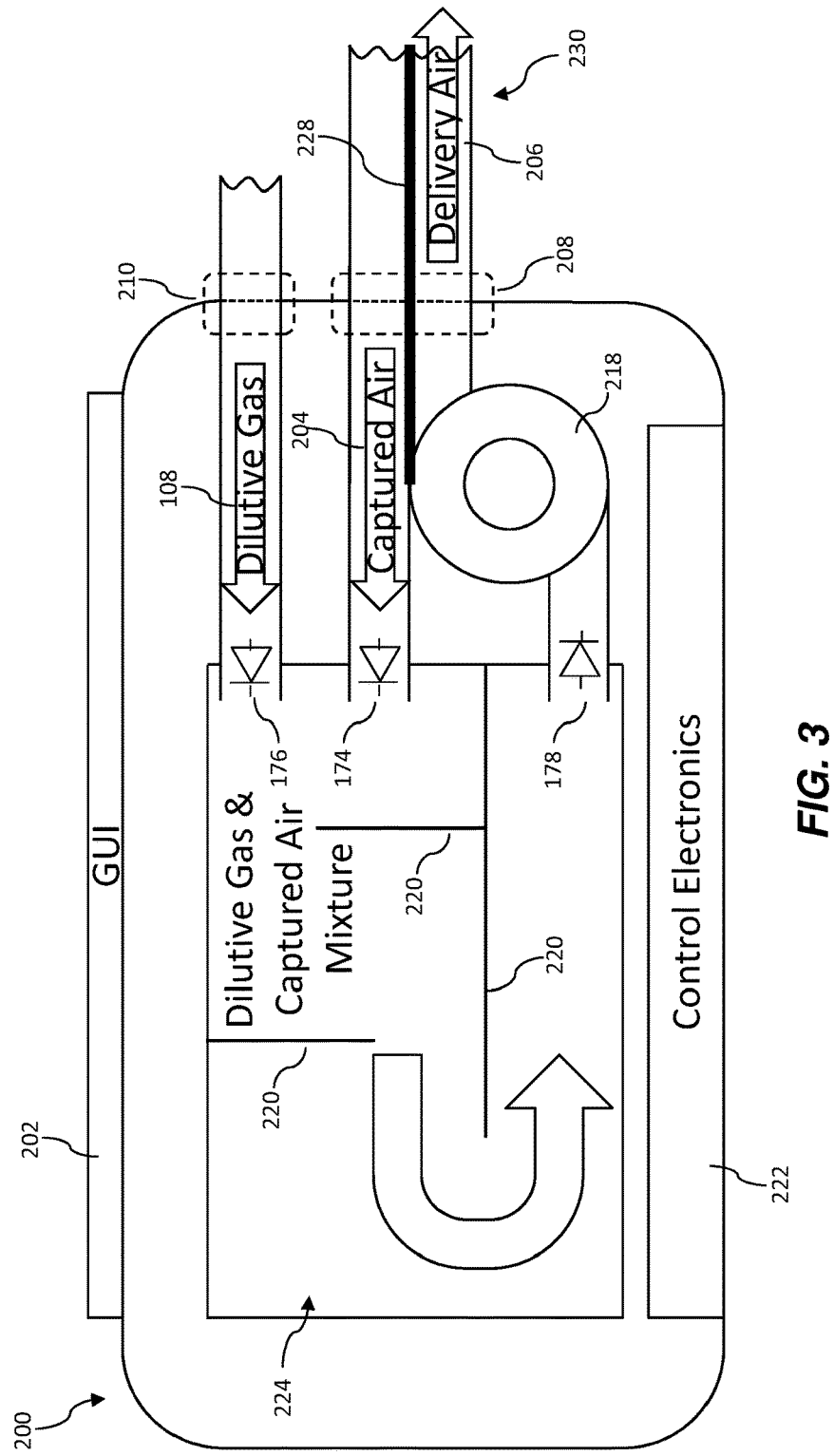
FIG. 3 Illustration of one embodiment of a positive airway pressure device with a mixing chamber for use in the present invention.

FIG. 3 illustrates in detail one embodiment of a positive airway pressure device with a mixing chamber for use in the present invention. In this preferred embodiment of PAP device 200, there is preferably an input/output port 208 for connecting the PAP device to the distal ends of both the capture and delivery devices. In this embodiment, the capture and delivery devices are represented by a single multi-lumened hose that may be used rather than separate hoses for capturing and delivering air. The purpose of a multi-lumened hose is to further increase subject comfort by decreasing interference with the subject while sleeping. A divider 228 in the multi-lumened hose as shown in FIG. 3, concentric hoses, or the like, preferably separate the capture and delivery devices into separate cavities of the multi-lumened hose. Preferably, the input/output port 208 is also "keyed" by offset depths for each cavity plug, different sized plugs for each cavity, or the like, so that the direction of airflow is properly aligned into and out of the PAP device 200 (i.e. captured air 204 enters the PAP device 200 and delivery air 206 leaves the PAP device 200). As previously described, captured air 204 from the distal opening of the air capture cavity of the capture device at the input/output port 208 and dilutive gas 108 from input port 210 are both connected to a mixing chamber 224 via regulatory valves 174, 176. Additionally, a pressurized air generator 218 is connected to the mixing chamber 224 via a regulatory valve 178. Preferably, when the valves 174, 176, 178 are open, the pressurized air generator helps to pull captured air 204 from the distal opening of the air capture cavity of the capture device at the input/output port 208 and dilutive gas 108 from the input port 210 through the mixing chamber where baffles 220 further induce mixing. The delivery air 206 then leaves through the distal opening of the air delivery cavity of the delivery device at input/output port 208. The regulatory valves 174, 176, 178 and pressurized air generator 218 are preferably controlled by control electronics 222, located within the PAP device 200, which analyze signals from sensors attached to the rebreathing circuit system and/or the subject. Sensors may include, but are not limited to, $CO_2$ sensors, airflow sensors, pneumotachographs, acoustic transducers, thermistors, pressure transducers, respiratory plethysmography belts, and the like for monitoring concentrations of air, airflow, and respiratory parameters. The control electronics 222 are preferably powered by either an internal power source such as a battery or an external power source such as a standard AC powered wall outlet. Additionally, the control electronics 222 preferably interact with a form of a graphical user interface (GUI) 202. The GUI may be a touch screen, a series of LEDs, buttons, and LCD displays, or the like. Interaction between the control electronics 222 and GUI 202 preferably allows the subject or clinician to set regulatory parameters such as carbon dioxide concentration ranges, pressure ranges, treatment protocols, and the like. The GUI 202 preferably also displays results from sensors located throughout the rebreathing circuit. For example, information displayed may include CO2 concentration of exhaled air per unit time, the subject's breathing parameters, and the like, as well as alerts of any errors within the PAP device 200 or system.

Figure 4:
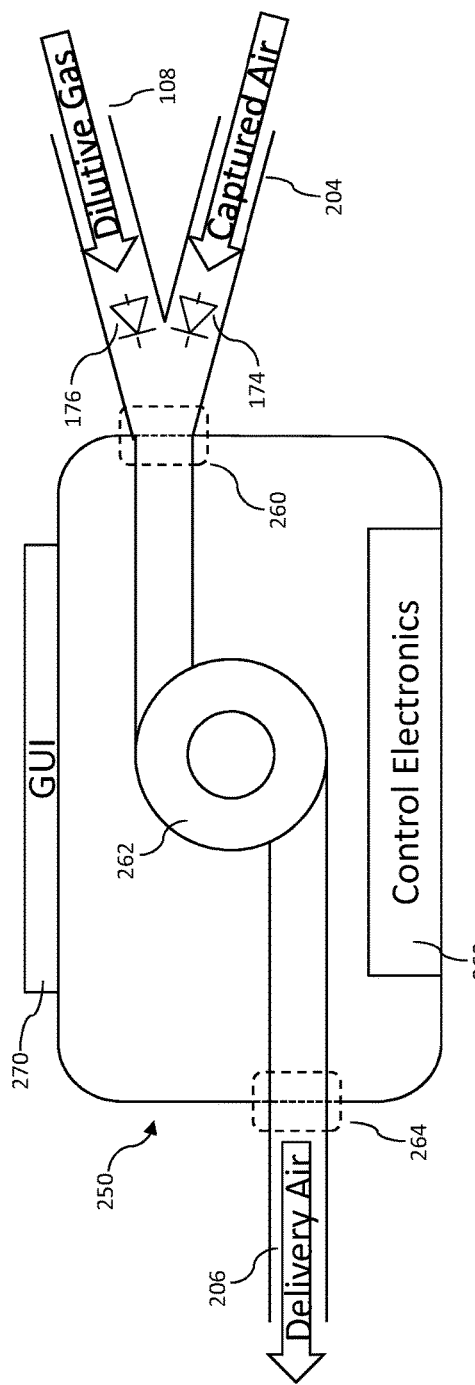
FIG. 4 Illustration of one embodiment of a positive airway pressure device with no mixing chamber for use in the present invention.

FIG. 4 illustrates one embodiment of the present invention of a positive airway pressure device with no mixing chamber. Unlike the PAP devices of FIGS. 2 and 3, the PAP device 250 of FIG. 4 has no mixing chamber. Captured air 204 from a capture device and dilutive gas 108 from ambient air or an external source are instead preferably connected via a y-connector to a single input port 260. Regulatory valves 174, 176 are preferably located at the junction of the y-connection, outside of the single input port 260 to control the volumes of both the captured air and dilutive gas that enter the PAP device 250. In other embodiments, the captured air 204 and dilutive gas 108 may each have separate input ports on the PAP device 250 with a y-connector inside the PAP device 250. As in various other embodiments, a pressurized air generator 262 preferably helps pull in captured air 204 from a capture device and dilutive gas 108 from an external source when respective regulatory valves 174, 176 are open. Without a separate mixing chamber, preferably the turbulence from the pressurized air generator 262 also induces mixing of the captured air 204 and dilutive gas 108 as they pass through the pressurized air generator 262. The delivery air 206 then exits through an output port 264. In this embodiment, control electronics 268 and a GUI 270 are also present and preferably interact with each other, the PAP device 250, regulatory valves 174, 176, a capture device, a delivery device, any external dilutive gas sources, and the system as a whole as previously described. It is to be understood that the above descriptions of preferred embodiments of PAP devices are merely exemplary and not wholly inclusive of full scope of the present invention. Other embodiments may incorporate the addition or removal of sensors, regulatory valves, GUIs, input and output ports, and the like known to one of ordinary skill in the art.

Figure 5:
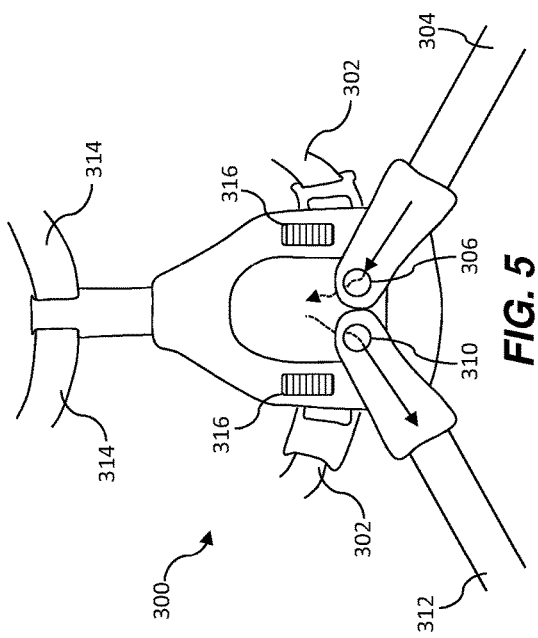
FIG. 5 Illustration of one embodiment of a mask for use in the present invention.

Moving now to FIG. 5, one embodiment of a mask for use in the present invention is illustrated. The oronasal mask 300 illustrated in FIG. 5 preferably covers both a subject's mouth and nose so as to physically provide the most respiratory coverage, however, other embodiments of a mask could cover only the nose, mouth only, or both with separate masks. Further, a mask could simply be a nasal cannula or mouthpiece rather than a full oronasal mask as depicted in the illustration of FIG. 5. The oronasal mask 300 of FIG. 5 is preferably held in position on a subject's head or face using at least one adjustable strap 302 or 314. More preferably, the oronasal mask 300 is meant to be rested and secured against a subject's forehead by an adjustable strap 314 as well as an adjustable strap 302 around the base of the head. Delivery air is preferably delivered to the oronasal mask 300 through the proximal opening of a delivery device 304 and attached to the oronasal mask 300 at a connection point 306 which allows the proximal opening of the delivery device 304 to swivel about the connection point 306 so the subject has greater freedom of movement during sleep.

Additionally, the connection is preferably airtight to prevent leaking and preferably contains a one-way valve to prevent backflow of delivery air or a subject's exhaled air from the mask back to the delivery device. Likewise, the proximal opening of a capture device 312 is preferably also attached to the oronasal mask 300 at a connection point 310. Preferably, the connection point 310 for the proximal opening of the capture device 312 contains all of the same properties as the connection point 306 for the proximal opening of the delivery device 304. A one-way valve, flow-based valve, or other regulatory valve known to those skilled in the art located at the connection point 310 for the proximal opening of the capture device preferably allows only a subject's exhaled air to pass through and prevents backflow of any captured air from the capture device back into the oronasal mask 300. Likewise, a one-way valve, flow-based valve, or other regulatory valve known to those skilled in the art located at the connection point 306 for the proximal opening of the delivery device 304 preferably allows only the delivery air to pass through and prevents backflow of any delivery air back into the delivery device. Although the connection points 306, 310 are shown adjacent one another, other embodiments may use other form factors, such as a single connection point or concentric connection points if the capture and delivery devices are similar to those discussed in FIG. 3 and use a multi-lumened hose and corresponding input/output port. In such embodiments, flow-based valves as described in FIGS. 10a and 10b; 11a and 11b; and 12 are preferably used to prevent dilution and backflow because both the delivery device and capture device can share a single port located on an oronasal mask while remaining isolated from each other. Preferably, the volume of space created between a subject's face and an the oronasal mask 300 collects delivery air after it leaves the proximal opening of a delivery device 304 but before it is inhaled by the subject, and collects a subject's exhaled air before it passes through the proximal opening of a capture device 312. The oronasal mask 300 shown in FIG. 5 also contains passive vents 316 so that pressure inside the mask remains passively regulated and thus more comfortable for the subject. In other embodiments of the present invention, vents may be omitted altogether, or may be controlled by an actuator, servo, or the like that acts according to signals from a processor responding to a feedback stimulus from sensors or user control. While a limited number of embodiments are described, it will be clear to one skilled in the art a mask of the present invention may take many forms.

Figure 6A:
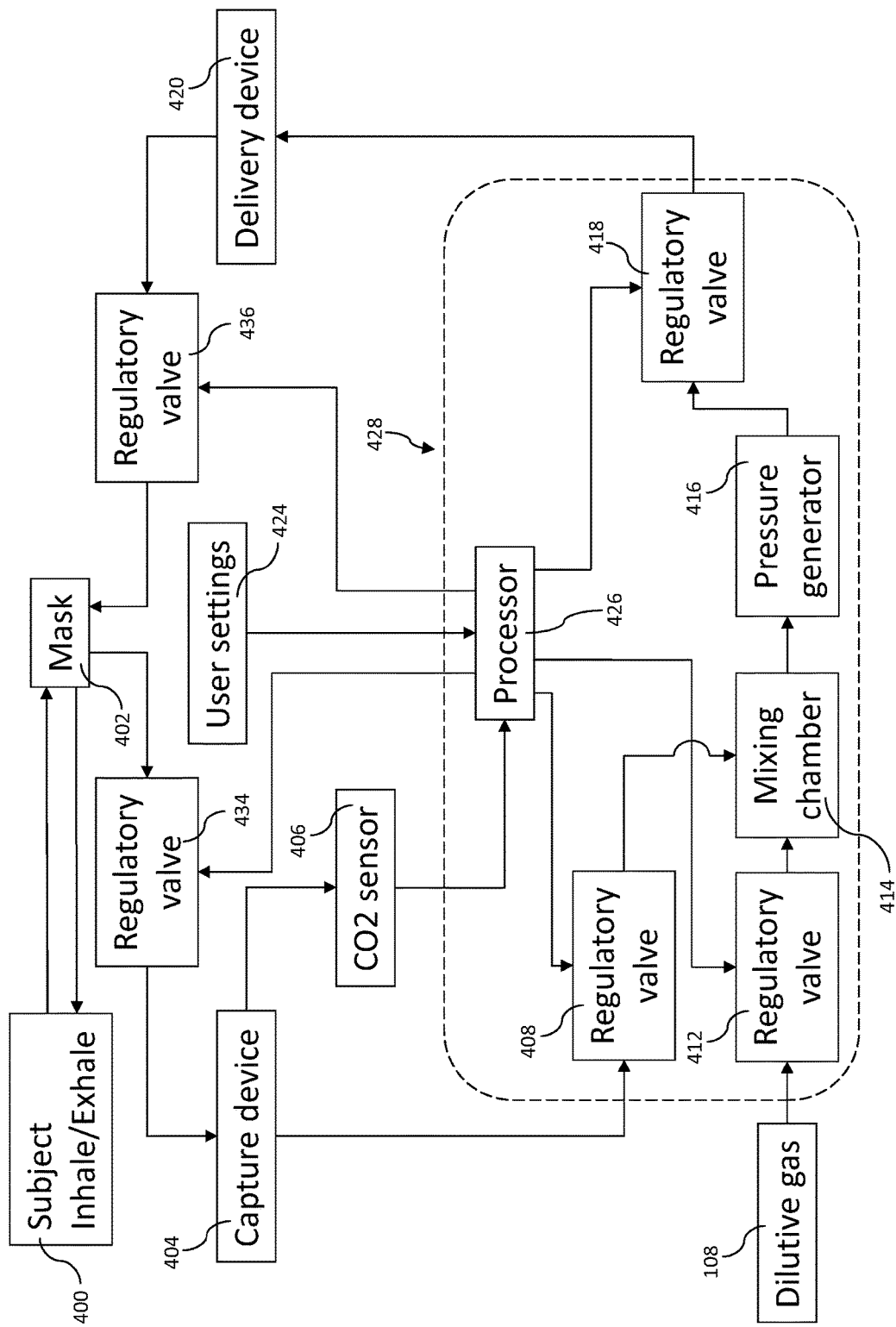
FIG. 6 Block diagrams illustrating the control and flow of air through the rebreathing circuit in two embodiments of the present invention.
Figure 6B:
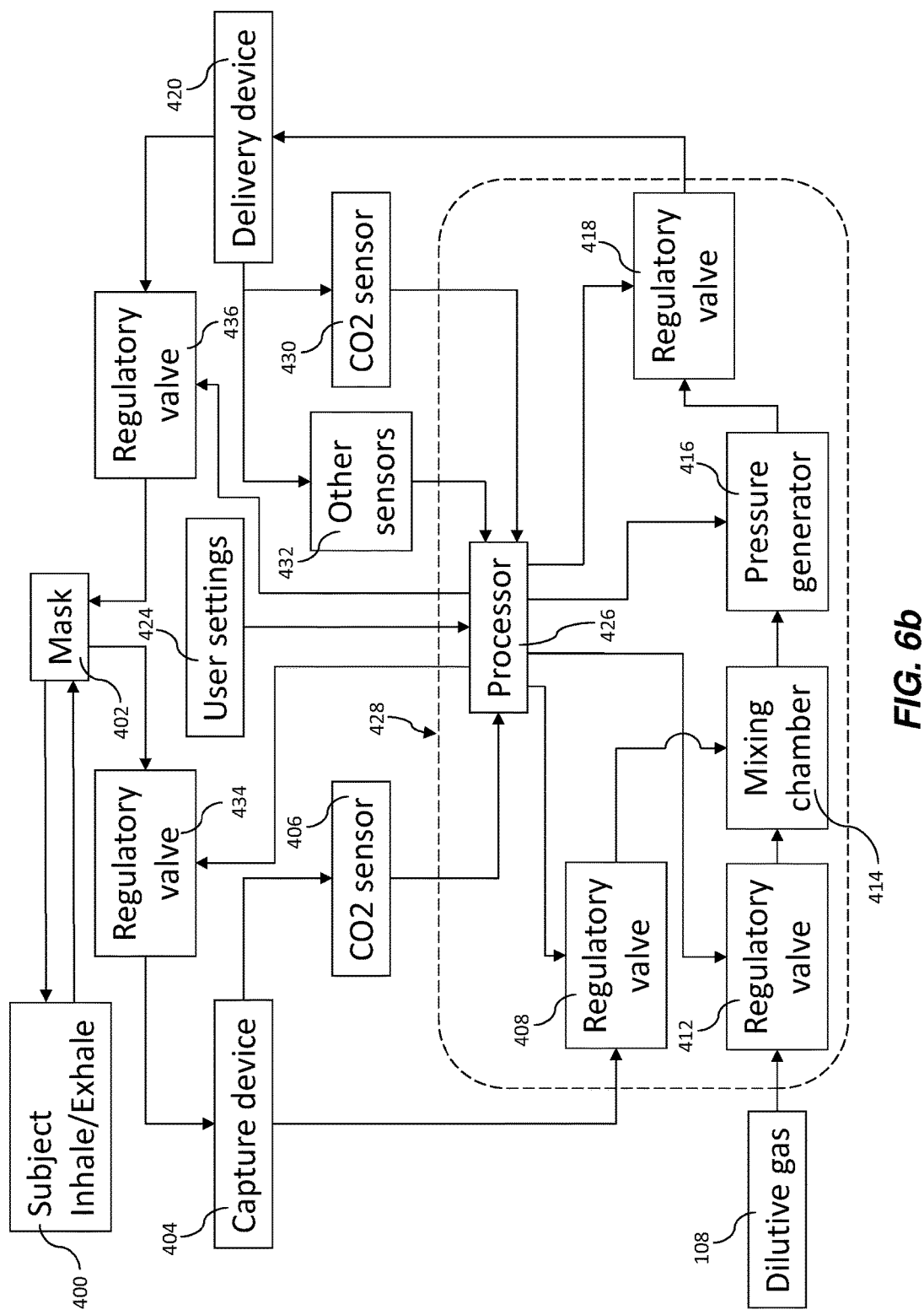

Moving now to FIGS. 6a and 6b, FIG. 6a is a block diagram of the control and flow of air through one embodiment of a rebreathing circuit of the present invention using no feedback controls, while FIG. 6b inserts a feedback mechanism into the diagram of FIG. 6a. Starting with FIG. 6a, initially as a subject exhales 400, the subject's exhaled air enters a subject's mask 402, connected to the proximal ends of both a capture device 404 and delivery device 420, where the exhaled air leaves through regulatory valve 434 to the proximal opening of the capture device 404. Preferably, the capture device 404 contains a carbon dioxide sensor 406 for determining the concentration of $CO_2$ in captured air. The CO2 sensor 406 sends signals to a processor 426, which exists as part of a series of control electronics within a PAP device 428, preferably uses signals from the CO2 sensor 406 along user settings 424 to control regulatory valves that control the volumes of captured air and dilutive gas 108 permitted to enter a mixing chamber 414. This regulation by the processor 426 controls the final carbon dioxide concentration of the delivery air. Other sensors (not shown) known to those skilled in the art such as pressure transducers, airflow sensors, thermistors, and the like, may also be used within the capture device 404 to determine desired mixing settings. Air then leaves the mixing chamber 414 and is pressurized in the pressure generator 416. Like regulatory valves 408, 412 at the PAP device 428 input, a regulatory valve 418 at the PAP device 428 output and regulatory valves 434, 436 at the mask 402 may be similarly regulated by a processor receiving input from a CO2 sensor 406, user settings 424, and other sensors (not shown). After leaving the PAP device 428, delivery air is preferably pushed into the distal opening of the delivery device 420 and then into the subject's mask 402 via regulatory valve 436 at the proximal opening of the delivery device 420. Once in the mask, the subject inhales 400 the delivery air.

Feedback mechanisms of FIG. 6b use a carbon dioxide sensor 430 and other sensors 432, such as pressure transducers, airflow sensors, thermistors, and the like, to monitor delivery air in the delivery device 420. The signals from the CO2 sensor 430 and other sensors 432 is input to the processor 426, which preferably uses these signals as a feedback check on the delivery air output by the PAP device 428. Analysis of these signals, along with the CO2 sensor 406 from the capture device 404 and user settings 424 allows the processor to better control each of the regulatory valves 408, 412, 418, 434, 436 as well as the pressure generator 416, to achieve the desired air pressure and carbon dioxide concentrations. While a limited number of embodiments are described, it will be clear to one skilled in the art the rebreathing circuit described may take many forms.

The sensors used in this process are preferably wireless, but may also be wired to the PAP device 428. Wireless forms may include optical or radio links such as Bluetooth®, IEEE 802.11 communication protocols, and the like. Wired connections are preferably contained within the appropriate capture and delivery devices, and are insulated to protect them from any moisture buildup as a result of condensation. Furthermore, they should be secured within the tubes to prevent movement due to the changes in air pressure within the tubes during use. Preferably they are both well protected and easily removable for cleaning Various sensors, as part of a control system just described, may also be located within the mask 402, mixing chamber 414, pressure generator 416, and the like, as a person skilled in the art may find it useful to measure air properties at various locations. Additionally, various sensors for measuring a subject's respiratory and breathing parameters may also be useful for regulating pressure and mixing concentrations. Such sensors known to those skilled in the art may include, but are not limited to, pneumotachographs, acoustic transducers, respiratory plethysmography belts, and the like, and would preferably be connected to the processor 426 of the PAP device 428 like those previously described.

Figure 7:
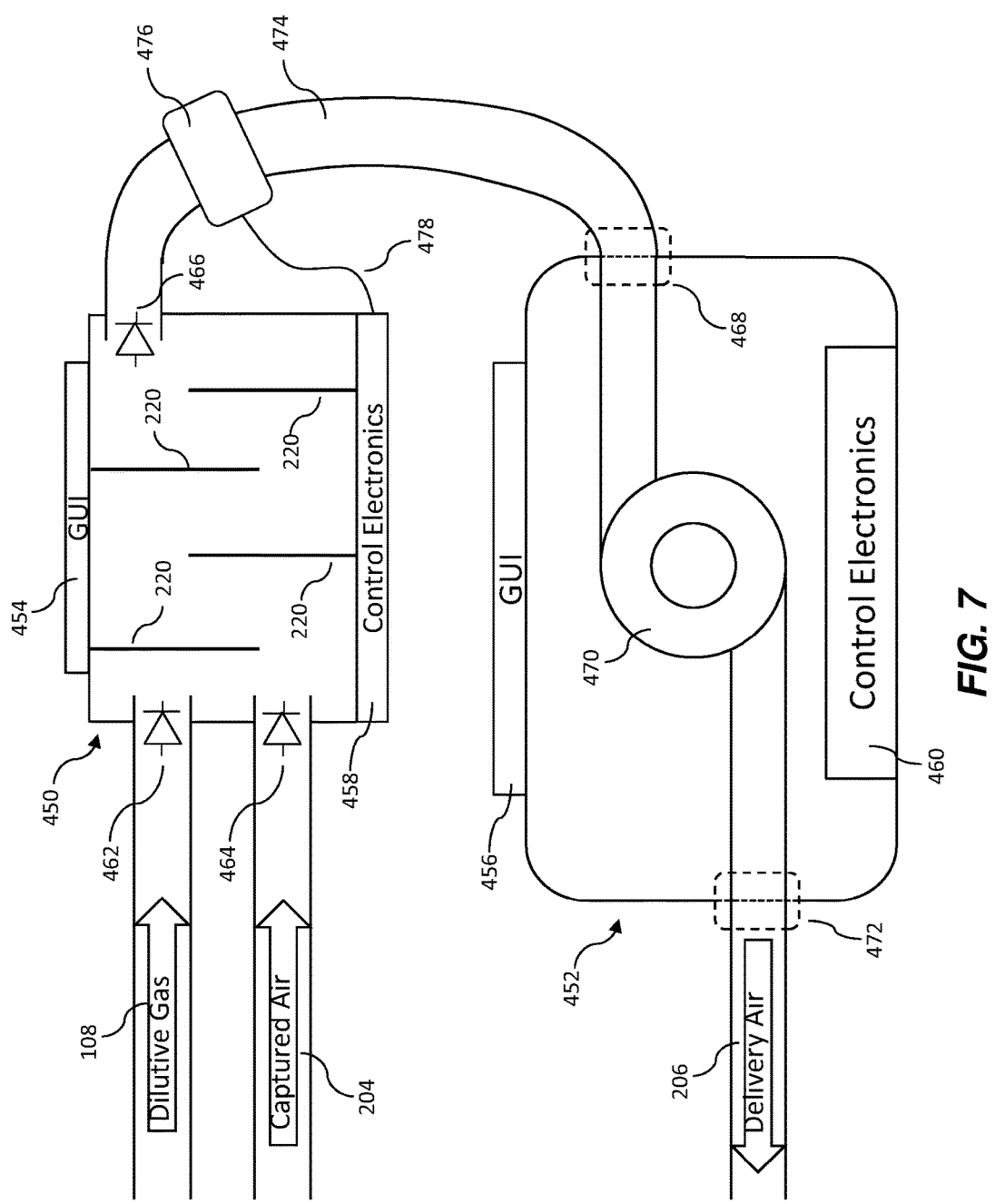
FIG. 7 Illustration of one embodiment of a positive airway pressure device with an external mixing chamber for use in the present invention.

FIG. 7 illustrates one embodiment of a positive airway pressure device with an external mixing chamber for use in the present invention. An external mixing chamber 450 preferably has two inputs, each controlled by regulatory valves 462, 464. These regulatory valves 462, 464 may be passive but are preferably controlled by actuators, servos, solenoids, or the like, which, in turn, are preferably controlled by control electronics 458 specifically designed for use with the mixing chamber 450. Preferably, regulatory valve 462 controls the input of dilutive gas 108 while the other regulatory valve 464 controls the input of captured air 204 into the mixing chamber 450. By controlling the input of both the dilutive gas 108 and captured air 204, the regulatory valves 462, 464 can preferably control the concentration of carbon dioxide in the delivery air 206 and prevent backflow of any air to the capture device (not shown) and dilutive gas source (not shown). While regulatory valves 462, 464 are illustrated in FIG. 7 as incorporated in the mixing chamber 450, these valves could also just as easily be located in the air capture hose (not shown) or the oronasal mask (not shown). Furthermore, in certain embodiments of the present invention a single valve, can be used in place of the two separate regulatory valves 462, 464 illustrated in FIG. 2. Baffles 220 are also preferably located inside the mixing chamber 450 in order to create turbulence and facilitate mixing between the dilutive gas 108 and captured air 204 as they pass through the mixing chamber 450. A regulatory valve 466 is also preferably located at the output of the mixing chamber and may be passive or controlled by the control electronics 458 as previously described. The control electronics 458 also preferably control a GUI 454 located on the mixing chamber 450. The GUI 454 is preferably similar to those previously described that are capable of receiving user input for manually adjusting mixing parameters and alerting users of any errors.

As mixed air leaves the mixing chamber 450 through regulatory valve 466, it preferably enters a connecting hose 474 that connects the output of the mixing chamber to the input port 468 of a PAP device 452. The connecting hose 474 preferably contains a carbon dioxide sensor 476 which may be connected via wire 478 to the mixing chamber's control electronics or wirelessly in other embodiments. A pressurized air generator 470 preferably draws the mixed air through the input port 468 of the PAP device 452. Delivery air 206, or pressurized mixed air, then leaves through the output port 472 of the PAP device 452 so that it can be inhaled by a subject via a delivery device (not shown). Similar to other embodiments, control electronics 460 of the PAP device 452 preferably use sensors such as carbon dioxide sensor 476 to control pressures generated by the air pressure generator 470, regulate the input port 468 and output port 472, and interact with the GUI 456 of the PAP device 452. The GUI preferably alerts a user to errors or warnings and receives input from the user regarding manual adjustment of the desired pressure of the delivery air 206 in a manner similar to PAP devices previously described. It is important to note that in the embodiment of the present invention shown in FIG. 7, the mixing chamber 450 and PAP device 452 are independent devices with independent control electronics 458, 460 and independent GUIs 454, 456. Therefore, the mixing chamber 450 and PAP device 452 are only physically connected by the connecting hose 474. In certain other embodiments, control electronics may be located solely in either the mixing chamber 450 or PAP device 452 and may then be connected to the various sensors and other components of the present invention either by wireless connections, traditional wired connections, or a combination of the two.

Figure 8:
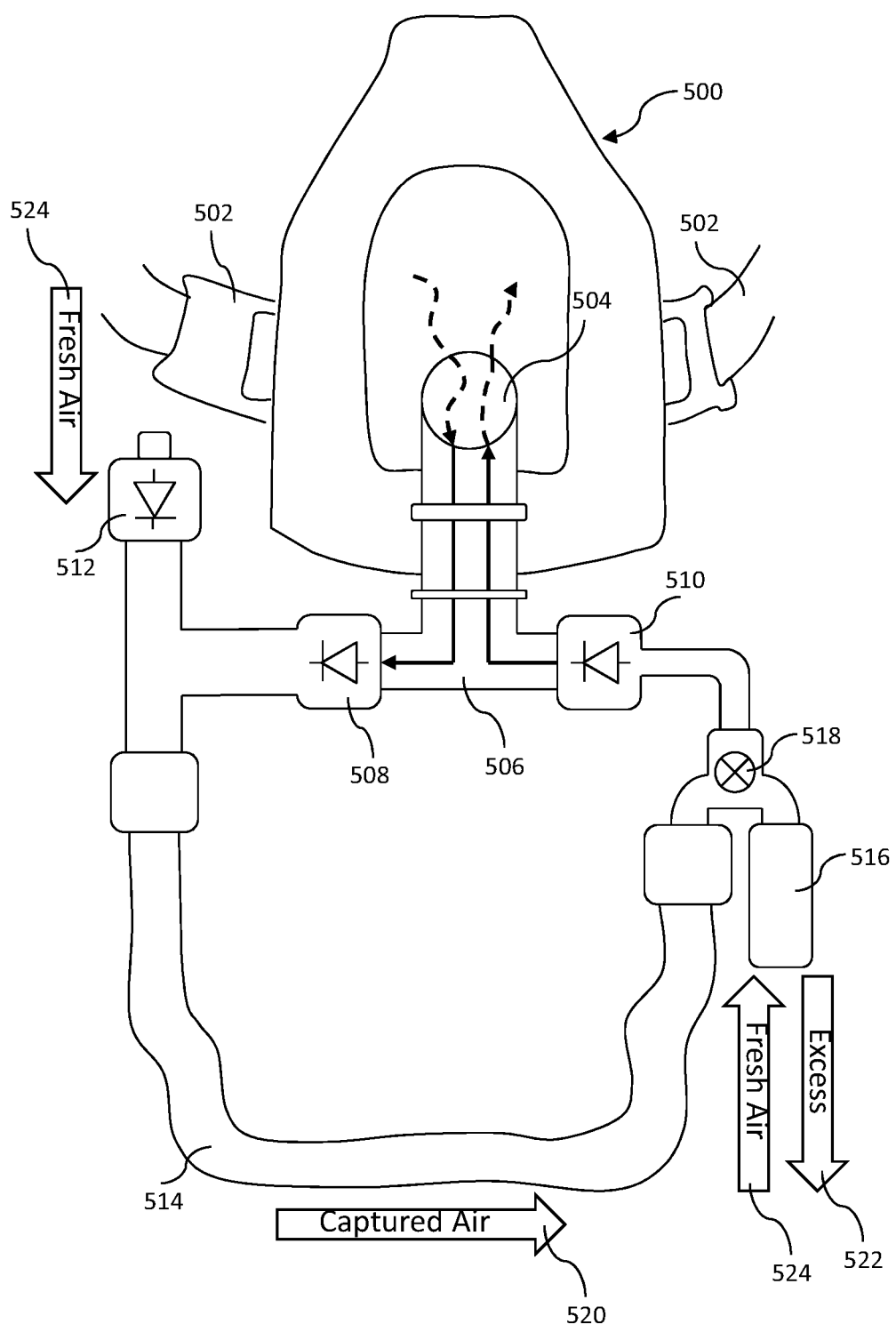
FIG. 8 Illustration of one embodiment of a passive rebreathing circuit of the present invention.

FIG. 8 illustrates an alternative embodiment of the present invention that utilizes a passive rebreathing circuit. By passive it is meant that the rebreathing circuit does not include a source of pressurized air, such as the CPAP device described above. In this embodiment, a subject wears an oronasal mask 500 secured to the head with a strap 502, set of straps (not shown), chinstrap (not shown), head band (not shown), adhesive (not shown), or the like. The front of the mask 500 preferably contains a single inhale/exhale port 504 allowing a subject to inhale air into the oronasal mask 500 and exhale air out of the oronasal mask 500. Preferably connected to the inhale/exhale port 504 of the oronasal mask 500 is a regulatory valve junction 506 containing two regulatory check valves 508, 510 for controlling air flow in a single direction (shown as counterclockwise in FIG. 8). As a subject exhales, the regulatory valve junction 506 forces the subject's exhaled air through regulatory check valve 508 and regulatory check valve 512 further requires the exhaled air to enter the capture device 514. As exhaled air becomes captured in the capture device 514, any excess captured air 520 may be expelled from the rebreathing circuit through a fresh air inlet 516. In the present embodiment, the capture device is a tube, however in other embodiments it may be a bellows, or other device capable of holding a volume of air. When a subject inhales, a regulatory valve 518 preferably controls the amount of fresh air 524 entering through a fresh air inlet 516 and captured air 520 that combine to become delivery air for the subject. Finally, regulatory check valve 510 allows the delivery air to enter the regulatory valve junction 506 and enter the inhale/exhale port 504 of the oronasal mask 500 so that the subject may inhale the delivery air. Regulatory check valve 512 allows fresh air 524 to backfill the capture device 514 as the subject inhales in order to prevent a vacuum, which would prevent delivery air from entering the oronasal mask 500. It will be understood that the number and types of regulatory valves illustrated in the passive rebreathing circuit of FIG. 7 are not intended to be a limiting description. For example, in other embodiments, regulatory check valves 508 and 512 may be combined as a swing check valve, or the like, which opens the capture device 514 to the regulatory valve junction 506 and prevents fresh air 524 from entering the capture device while a subject exhales; when the subject inhales, the combined swing check valve would open the capture device 514 to the fresh air 524 and close the capture device 514 to the regulatory valve junction 506. Furthermore, check valves 506, 508, and 510 could be replaced by a flow-based valve, as shown in FIGS. 10*a* and 10*b*; 11*a* and 11*b*, and 12, containing ports for a delivery device, capture device, and oronasal mask. Such valves are able to control air flow in two directions as described below in order to prevent dilution in the captured air with delivery air. The various valves used in this embodiment and others may be passive valves or, in certain embodiments, actively controlled by electronics.

Figure 9:
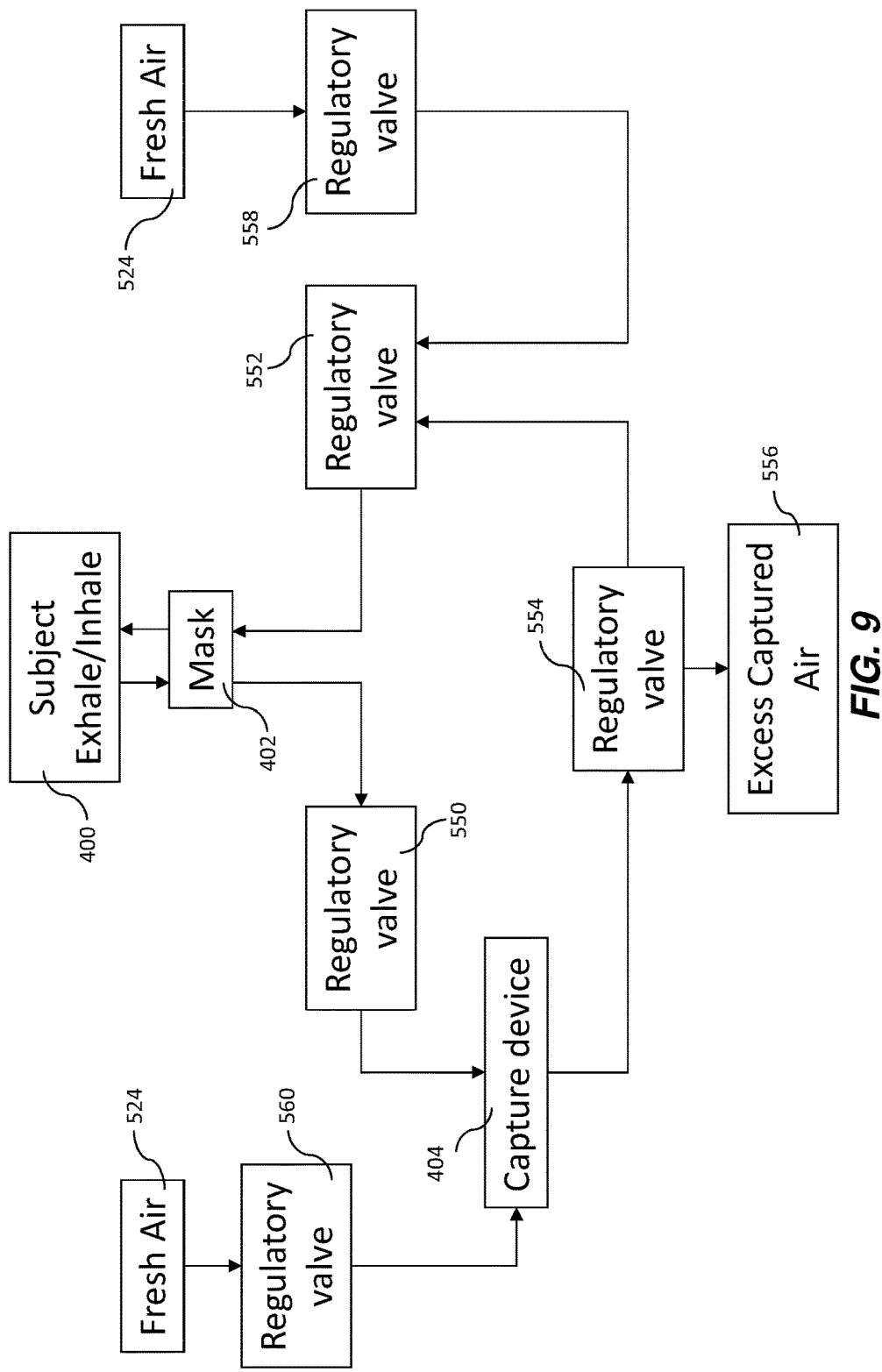
FIG. 9 Block diagram illustrating the flow of air through a passive rebreathing circuit of the present invention.
Figure 12:
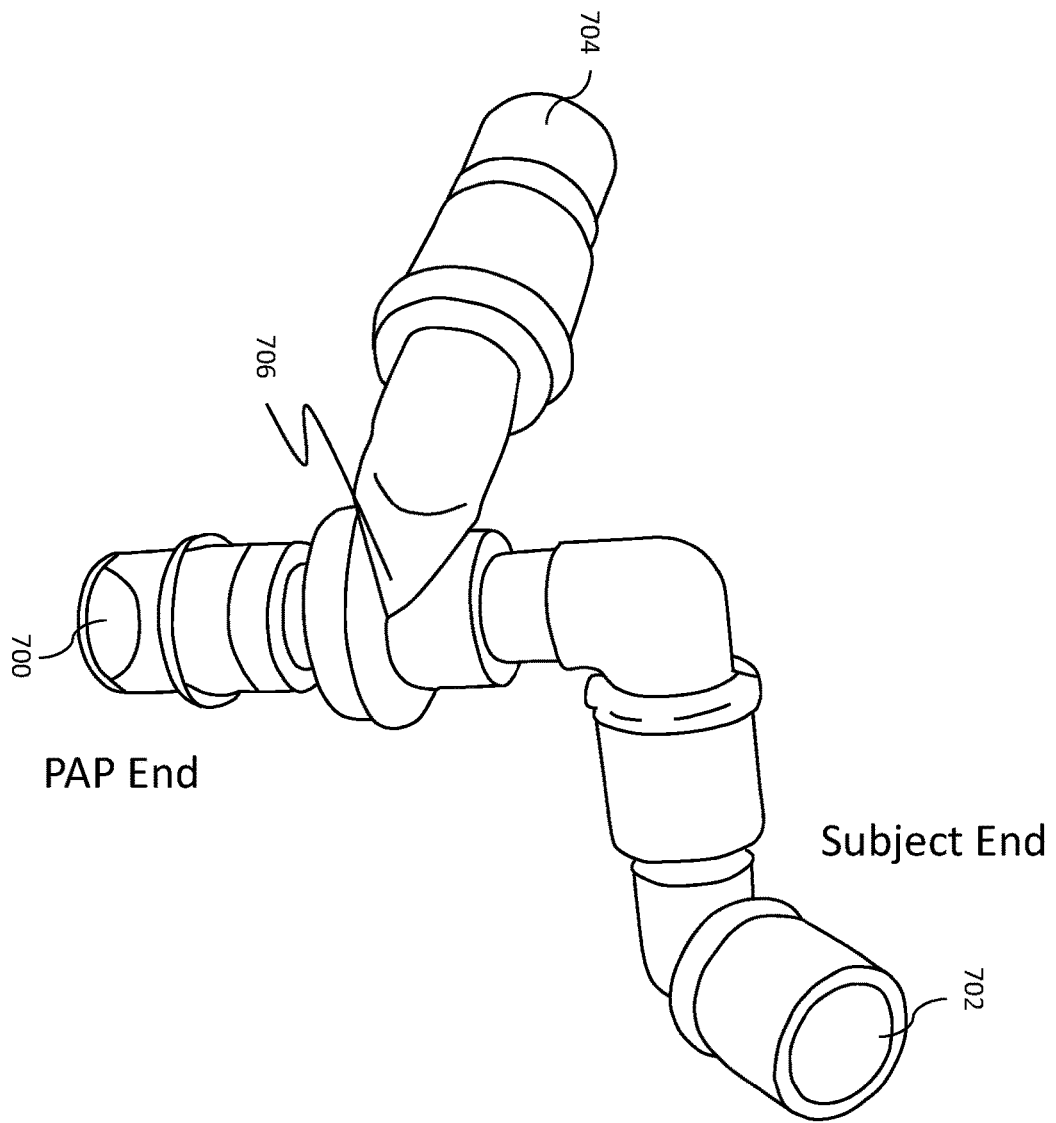
FIG. 12 Illustration the implementation of a flow-based regulatory valve with tubes and connectors as it might be used in the present invention.

FIG. 9 shows a block diagram illustrating the flow of air through a passive rebreathing circuit of the present invention similar to the embodiment illustrated in FIG. 8. Initially as a subject exhales 400, the subject's exhaled air enters a mask 402 worn by the subject. The exhaled air is then forced to through a regulatory valve 550 that is designed to control the directional flow of the subject's exhaled air. In many embodiments, this regulatory valve 550 is a passive check valve or flow-based valve, however, it may also be controlled electronically through the use of servos in order to match the subject's breathing cycle, or combined with other regulatory valves as described below. After the subject's exhaled air passes through the regulatory valve 550, it is captured in a capture device 404. As already discussed above, the type and size of this capture device can vary according to the needs of individual subjects. As the capture device 404 fills with captured exhaled air, regulatory valve 554 allows excess captured air to leave the rebreathing system while preventing atmospheric or surrounding air from entering. Again, regulatory valve 554 may be a passive check valve, actively controlled check valve, swing check valve, relief valve, or the like. As the subject inhales 400, delivery air enters the subject's mask 402 through regulatory valve 552 which controls the directional flow of air through the rebreathing circuit. The delivery air is preferably a combination of fresh air 524 and captured air from the capture device 404. The fresh air 524 preferably enters the rebreathing circuit through an adjustable regulatory valve and mixes with the captured air before entering the subject's mask 402 via regulatory valve 552. In order to prevent a vacuum, fresh air 524 also enters the capture device 404 as the subject inhales 400. Again, the fresh air 524 must pass through a regulatory check valve so that it may only enter the rebreathing circuit and no other air may leave the rebreathing circuit. Lastly, it should be reiterated that in many embodiments, regulatory valves 550, 552, 554, 558, and 560 may be combined to simplify the rebreathing circuit. For example, regulatory valves 550 and 560 may be combined into a single swing check valve as described in FIG. 8. Valves 550 and 552 may also be combined in a single flow-based valve as described in FIGS. 10a and 10b; 11a and 11b; and 12. Additionally, regulatory check valves 554 and 558 may be combined into a single adjustable regulatory valve also illustrated by reference character 518 of FIG. 8. Again, the above combinations of valves are merely exemplary and are in no way intended to be a limiting description.

While the examples illustrated in FIGS. 8 and 9 do not include electronics or electronic sensors, it will nevertheless be understood that in certain preferred embodiments of the present invention such sensors could also be integrated into the passive rebreathing circuit illustrated in FIGS. 8 and 9. Such sensors could include, for example, flow sensors, carbon dioxide sensors, snore sensors, temperature sensors, oxygen sensors, and the like. If such electronic sensors, actively-controlled electronic valves, or other electronic components are used with the passive rebreathing circuit, the device preferably further includes at least a power source, digital memory, and a microprocessor which can be used to control and manage these various electronic components. If an electronic version of the passive rebreathing circuit is implemented, it preferably includes features such as the ability to set threshold concentrations of $CO_2$ and then allow the electronic components to maintain a specified level of $CO_2$ concentration within a desired range of accuracy.

FIGS. 10a and 10b; 11a and 11b; and 12 illustrate embodiments of a flow-based regulatory valve that may be used throughout the present invention. FIG. 10a shows the state of the flow-based regulatory valve while air travels from a positive airway pressure device to a subject. In this embodiment, the flow-based regulatory valve contains three ports: (1) a distal port 600, preferably connected to a positive airway pressure device (not shown) or other delivery device (not shown); (2) a proximal port 602 preferably connected to an oronasal mask, nasal cannula, or the like, attached to a subject; and (3) a capture port 604 preferably connected to a capture device for capturing a subject's exhaled air. As a PAP device pushes air through a delivery device, the pressurized air preferably enters the flow-based regulatory valve through the distal port 600 and forces the valve action 606 to move towards the proximal port 602 until it reaches proximal stops 608. The proximal stops 608 are preferably located on the proximal port 602 side of the capture port 604 such that the valve action 606, when forced against proximal stops 608, completely covers the capture port 604 but not the bottom pathway 610. The pressurized air from the PAP device can then preferably be routed through the bottom pathway 610 and leave the flow-based regulatory valve through the proximal port 602. FIG. 10b illustrates a similar mechanism when exhaled air from the subject enters the flow-based regulatory valve through the proximal port 602. When a subject exhales, air preferably enters the flow-based regulatory valve through the proximal port 602, forcing the valve action 606 to move towards the distal stops 612. The distal stops 612 are preferably located on the distal port 600 side of the capture port 604 such that the valve action 606, when forced against distal stops 612, completely opens the capture port 604 and completely covers the distal opening of the bottom pathway 610. With this mechanism, exhaled air preferably leaves the flow-based regulatory valve through the capture port 604.

While FIGS. 10a and 10b illustrate one embodiment of a flow-based regulatory valve, it will be clear to one skilled in the art a flow-based regulatory valve like that in FIGS. 10a and 10b may take many forms. For example, the valve action 606 may be biased by a spring attached to either the proximal stops 608 or distal stops 612. When attached to the proximal stops 608 or the distal stops 612, the valve action 606 could have a default resting position against the distal stops 612, thereby creating a default airflow pathway from the proximal port 602 through the collection port 604, or the valve action 606 could have a default resting position against the proximal stops 608, thereby creating a default airflow pathway from the distal port 600 through the proximal port 604. Still other embodiments may contain one-way valves within the flow-based regulatory valve. For example, a one-way valve may be located in the bottom pathway 610 or at the collection port 604. A one-way valve in the bottom pathway 610 would preferably further prevent backflow from the proximal port 602 through the distal port 600. A one-way valve located at the collection port 604 would likewise preferably further prevent backflow from a collection device to the proximal port 602.

FIGS. 11a and 11b illustrate another embodiment of a flow-based regulatory valve that may be used throughout the present invention. FIG. 11a illustrates the state of the flow-based regulatory valve as delivery air is passed from a PAP device (not shown) to a subject (not shown). Like the embodiment shown in FIGS. 10a and 10b, the flow-based regulatory valve contains three ports: (1) a distal port 650, preferably connected to a positive airway pressure device (not shown) or other delivery device (not shown); (2) a proximal port 652 preferably connected to an oronasal mask, nasal cannula, or the like, attached to a subject; and (3) a capture port 654 preferably connected to a capture device for capturing a subject's exhaled air. As shown in FIG. 11a, when delivery air from a PAP device enters the distal port 650 of the flow-based regulatory valve, the pressure of the air preferably opens a swinging valve action 656, thereby closing access to the capture port 654 and allowing delivery air to pass through the proximal port 652 and on to a subject. As shown in FIG. 11b, when a subject exhales, exhaled air preferably enters the proximal port 652 of the flow-based regulatory valve and is diverted by a closed swinging valve action 656 (in its resting position) to the capture port 654 where the exhaled air can be captured by a capture device (not shown). The swinging valve action 656 may take many forms and may be biased in either direction or to a middle point. Furthermore, the swinging valve action 656 may have a complex shape with multiple surfaces such that the surface that closes distal port 650 and the surface that closes proximal port 654 are distinctly different surfaces. Still furthermore, the swinging valve action 656 may be comprised of multiple interconnected components that work together through gears, pulleys, pivot points, springs or other mechanisms known to one skilled in the art.

Rather than showing the internal mechanisms as in FIGS. 10a and 10b, and 11a and 11b, FIG. 12 illustrates the implementation of a flow-based regulatory valve with hoses and connectors as it might be used in the present invention. Preferably, distal port 700 can be connected to tubes or hoses that are part of a PAP or delivery device. Likewise, proximal port 702 preferably connects at an oronasal mask, nasal cannula, or the like, or to tubes or hoses which connect to an oronasal mask, nasal cannula, or the like. Finally, capture port 704 preferably connects to tubes or hoses that are part of a capture device. The valve action 706, a swinging valve action in the present embodiment, is preferably located at the junction of all three ports.

It will be apparent to those of ordinary skill in the art that various modifications and variations can be made to the present invention as described above without departing from the spirit and scope of the invention. Thus, it is intended that the present invention cover the modifications and variations of this invention provided they come within the scope of the appended claims and their equivalents.

What I claim is:

1. A sleep-related breathing disorder treatment system comprising:
    a capture device for capturing exhaled air from a subject;
    a positive airway pressure (PAP) device with at least one gas inlet port and a gas outlet port, the at least one gas inlet port for receiving the capture exhaled air from the subject, and the PAP device for mixing and pressurizing the captured exhaled air and a dilutive gas to a pressure that is greater than atmospheric pressure; and
    a delivery device connected to the gas outlet port for delivering the pressurized mixture of at least the captured exhaled air and dilutive gas from the PAP device to the subject, wherein the delivery device completes a rebreathing circuit from the capture device through the PAP device to the subject.

2. The system of claim 1, wherein the system is adapted so the gas delivered to the subject using the PAP device has a concentration of between 0.01 and 5.0 percent $CO_2$, and the accuracy of the concentration of the $CO_2$ delivered to the subject is within 10 percent of a desired concentration.

3. The system of claim 2, comprising at least two regulatory valves at both a proximal and a distal end of the capture device.

4. The system of claim 1, wherein the delivery device and the capture device comprise in part separate chambers of a multi-lumened hose with the delivery device chamber connected to the gas outlet port and the capture device chamber connected to the gas inlet port.

5. The system of claim 1, the delivery device further comprising a mask and a hose, the mask further comprising two regulatory valves, one for connecting to the hose and receiving the mixed gas from the PAP through the hose, and the other adapted for passing exhaled air into the capture device.

6. The system of claim 1, the system further comprising, a processor and the capture device further comprising a $CO_2$ sensor with a signal for measuring the $CO_2$ concentration of exhaled air within the capture device and a regulatory valve adjusted by the processor based in part on the signal from the $CO_2$ sensor.

7. A method for treating sleep-related breathing disorders comprising the steps of:
    capturing exhaled air from a subject;
    providing the captured exhaled air from the subject to a positive airway pressure (PAP) device;
    mixing the captured exhaled air and a dilutive gas in controlled quantities; and
    providing the mixture of at least captured exhaled air and dilutive gas to the subject using the PAP device to complete a rebreathing circuit.

8. The method of claim 7, wherein the mixed gas delivered to the subject using the PAP device has a concentration of between 0.01 and 5.0 percent $CO_2$, and the accuracy of the concentration of the $CO_2$ delivered to the subject is within 10 percent of a desired concentration.

9. The method of claim 8, further including the steps of measuring the captured exhaled air is with a $CO_2$ sensor having a signal for measuring the $CO_2$ concentration of exhaled air and regulating the exhaled air provided to the PAP device is with a processor based in part on the signal from the $CO_2$ sensor.

10. The method of claim 9, wherein the mixed gas is provided to the subject with a mask and a hose, the mask further comprising two regulatory valves, one for connecting to the hose and receiving the mixed gas from the PAP through the hose, and the other adapted for passing exhaled air hack to the PAP device.

11. The method of claim 7, wherein the during the step of capturing exhaled air from a subject a $CO_2$ sensor with a signal further measures the $CO_2$ concentration of exhaled air and the exhaled air provided to the PAP device is regulated with a processor and a valve based in part on the signal from the $CO_2$ sensor.

12. The method of claim 7, wherein the step of mixing is performed in part using baffles in the PAP device.

13. A positive airway pressure (PAP) device comprising:
    a mixing chamber further comprising a number of baffles for mixing at least a subject's exhaled air and a dilutive gas in controlled quantities;
    a pressurized air generator;
    an input port for passing the subject's exhaled air into the mixing chamber; and
    an output port for passing of a mixture of at least the subject's exhaled air and a dilutive air out of the PAP device using at least in part the source of pressurized air for delivery to a subject.

14. The device of claim 13 wherein the PAP device is adapted so the gas delivered to the subject has a concentration of between 0.01 and 5.0 percent $CO_2$, and the accuracy of the concentration of the $CO_2$ delivered to the subject is within 75 percent of a desired concentration.

15. The device of claim 14, further including a delivery device comprising a mask and a hose, the mask further comprising two regulatory valves, one for connecting to the hose and receiving the mixed gas from the output port through the hose, and the other adapted for passing exhaled air to the input port on the PAP device.

16. The device of claim 15, wherein the hose connected to the mask and to the outlet port on the PAP device is a multi-lumened hose with two chambers one chamber connected to the PAP device input port for delivering exhaled air to the PAP device from the mask and other chamber connected to the output port of the PAP device for delivering mixed gas to the mask.

17. The device of claim 14, wherein the accuracy of the concentration of the $CO_2$ delivered to the subject is within 10 percent of a desired concentration.

18. The device of claim 13, further comprising a second input port and a source of medical grade gas for inputting into the mixing chamber of the PAP device.

19. The device of claim 13, further comprising a display for displaying the amount of carbon dioxide included in the mixture of at least the subject's exhaled air and atmospheric air.

* * * * *